US011744665B2

(12) United States Patent
Nguyen et al.

(10) Patent No.: US 11,744,665 B2
(45) Date of Patent: Sep. 5, 2023

(54) MODULAR WORKSPACE PLATFORM SYSTEM, ACCESSORIES THEREFOR, AND ASSOCIATED METHODS

(71) Applicant: The Quick Co, LLC

(72) Inventors: Jack Chien Nguyen, Denver, CO (US); Marc Andrew Hanchak, Denver, CO (US); Peter Schuyler Livingston, Denver, CO (US)

(73) Assignee: The Quick Co, LLC, Denver, CO (US)

( * ) Notice: Subject to any disclaimer, the term of this patent is extended or adjusted under 35 U.S.C. 154(b) by 253 days.

(21) Appl. No.: 16/706,072

(22) Filed: Dec. 6, 2019

(65) Prior Publication Data

US 2020/0253680 A1 Aug. 13, 2020

Related U.S. Application Data

(60) Provisional application No. 62/804,725, filed on Feb. 12, 2019.

(51) Int. Cl.
*A61B 50/30* (2016.01)
*A61B 50/20* (2016.01)
*A61B 50/00* (2016.01)

(52) U.S. Cl.
CPC .............. *A61B 50/20* (2016.02); *A61B 50/30* (2016.02); *A61B 2050/002* (2016.02); *A61B 2050/3008* (2016.02)

(58) Field of Classification Search
CPC ..... A61C 19/006; A61C 19/001; A61B 50/20; A61B 50/30; A61B 2050/002; A61B 2050/3008

USPC ........................................... 206/438; 433/163
See application file for complete search history.

(56) References Cited

U.S. PATENT DOCUMENTS

| 4,976,615 | A | * | 12/1990 | Kravitz | .................... A61C 3/04 433/102 |
| 4,988,296 | A | * | 1/1991 | Spencer | ............... A61C 19/006 128/852 |
| 5,353,974 | A | * | 10/1994 | Maurizio | ................... A45F 5/00 224/183 |
| 5,368,482 | A | * | 11/1994 | Johnsen | ................. A61C 19/00 206/63.5 |
| 5,749,730 | A | * | 5/1998 | Johnsen | ................... B65D 1/36 433/163 |
| 6,257,888 | B1 | * | 7/2001 | Barham | ............... A61C 19/006 206/63.5 |

(Continued)

OTHER PUBLICATIONS

International Search Report, US1964971'dated Mar. 18, 2020.
Written Opinion, US1964971—dated Mar. 18, 2020.

*Primary Examiner* — Steven A. Reynolds
(74) *Attorney, Agent, or Firm* — Neugeboren O'Dowd PC

(57) ABSTRACT

A modular workspace platform system for providing a mobile work surface for a user includes a workspace platform attachable to a location specified by the user. The workspace platform includes a compact work surface for use in performing at least one manual task including temporarily storing a material, mixing two or more materials, temporarily supporting a tool, and providing a tool cleaning surface. In an embodiment, the compact work surface includes at least one of a trough, a tapered channel, a tool insertion slot, a wipe holder, a textured surface configured as the tool cleaning surface, a mixing surface a ruler holder, and a matrix ring holder.

18 Claims, 16 Drawing Sheets

(56) References Cited

U.S. PATENT DOCUMENTS

| | | | |
|---|---|---|---|
| 6,986,924 B2* | 1/2006 | Croll | A61C 19/006 428/40.1 |
| 7,946,848 B2* | 5/2011 | Discko, Jr. | A61C 19/006 433/163 |
| 8,517,233 B2* | 8/2013 | Podda-Heubach | A61B 90/53 224/267 |
| 2006/0166170 A1 | 7/2006 | Masters | |
| 2006/0226032 A1 | 10/2006 | Zalsman | |
| 2007/0283515 A1 | 12/2007 | Viscomi et al. | |
| 2008/0311543 A1* | 12/2008 | Viscomi | A61C 19/002 433/163 |
| 2011/0229843 A1 | 9/2011 | Oien et al. | |
| 2017/0325922 A1* | 11/2017 | Kandel | A61C 19/006 |
| 2018/0303590 A1* | 10/2018 | Luman | A61L 2/18 |

* cited by examiner

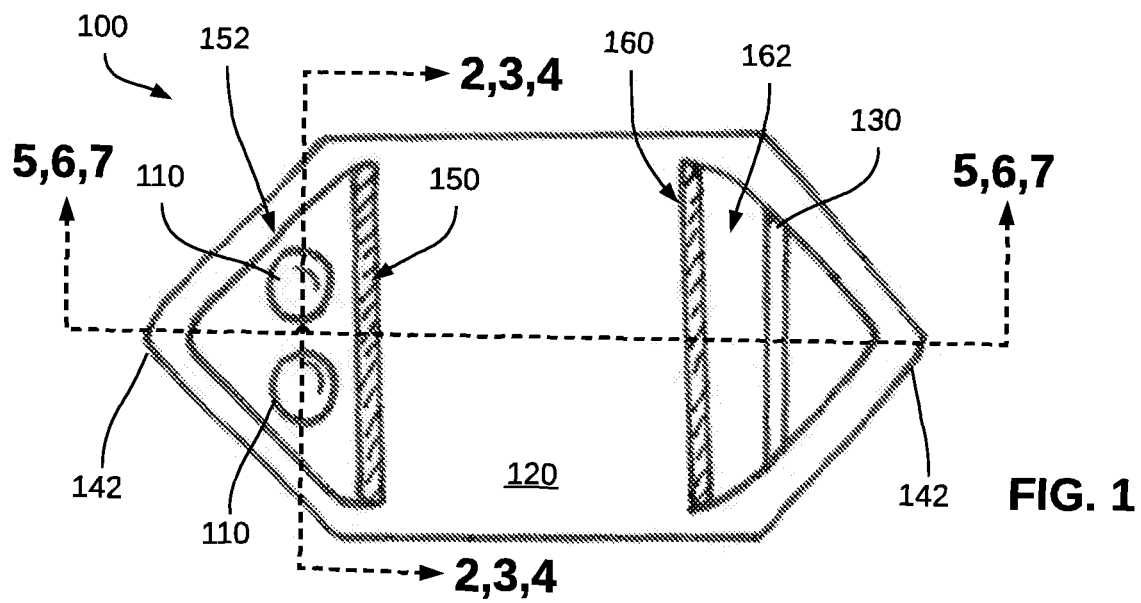
FIG. 1
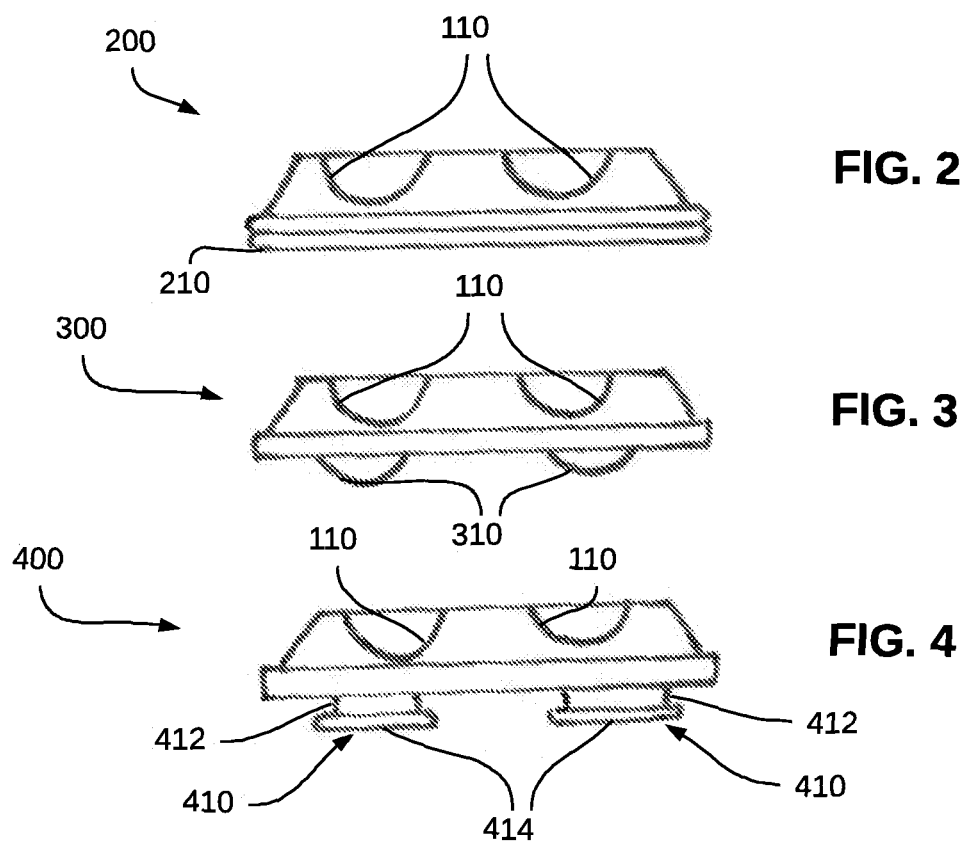
FIG. 2
FIG. 3
FIG. 4

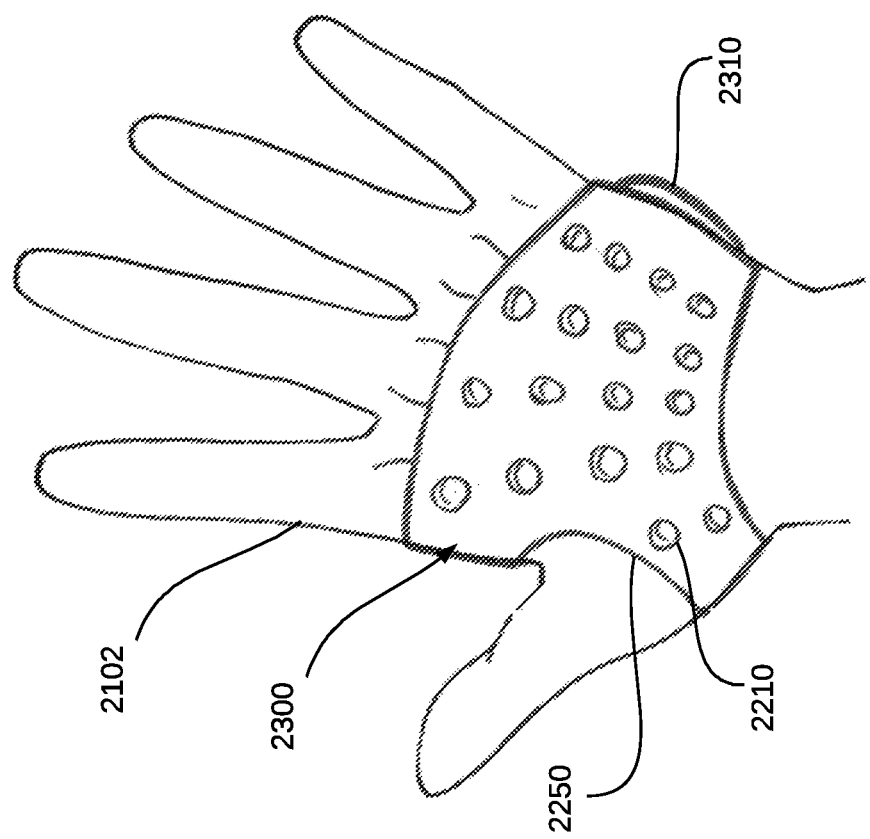
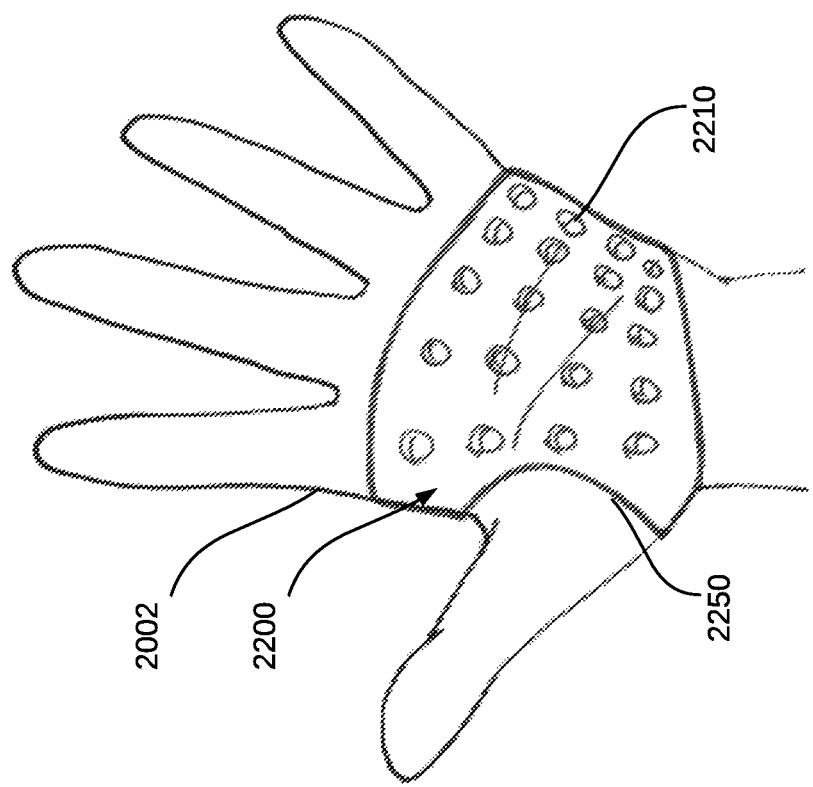

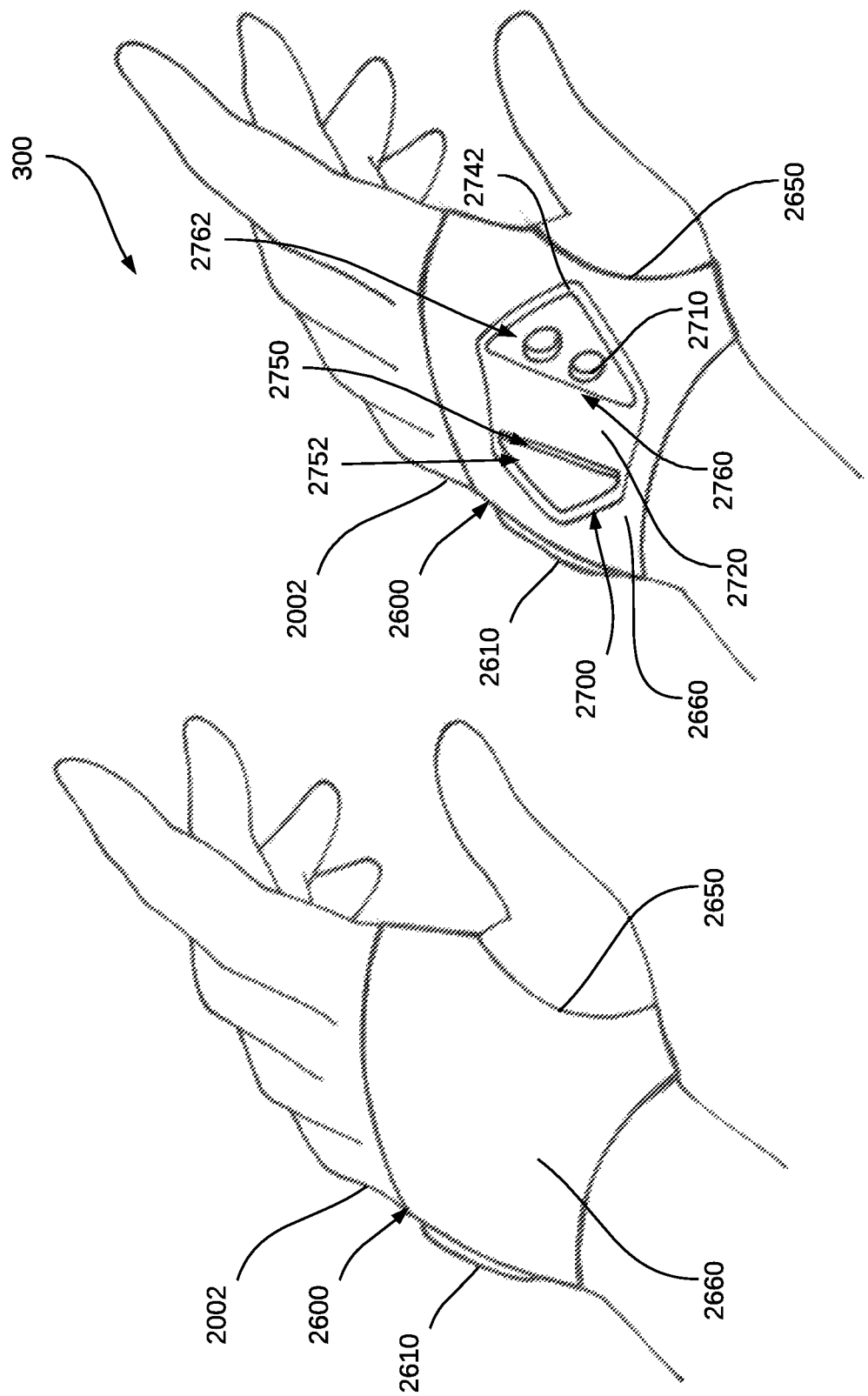

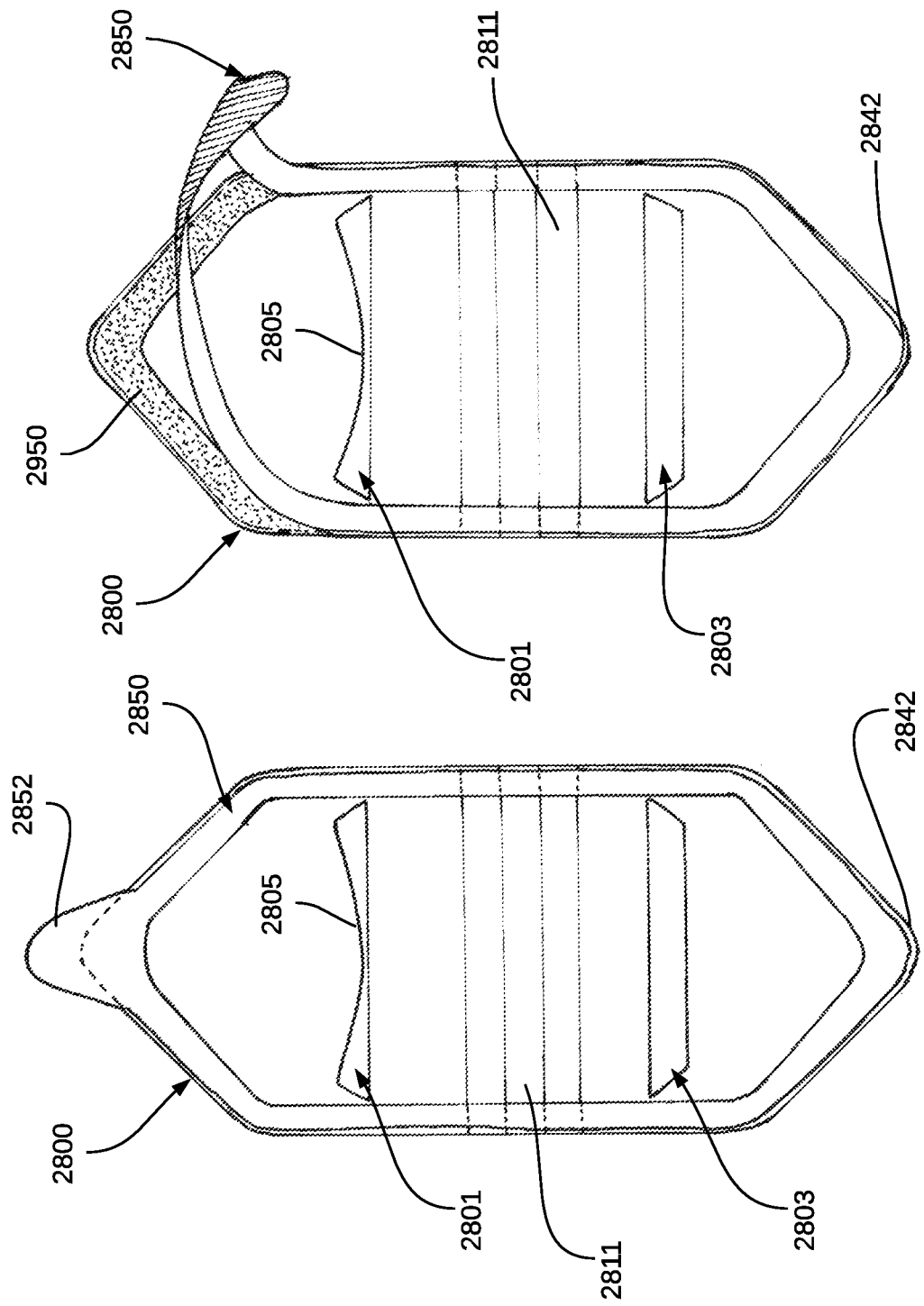

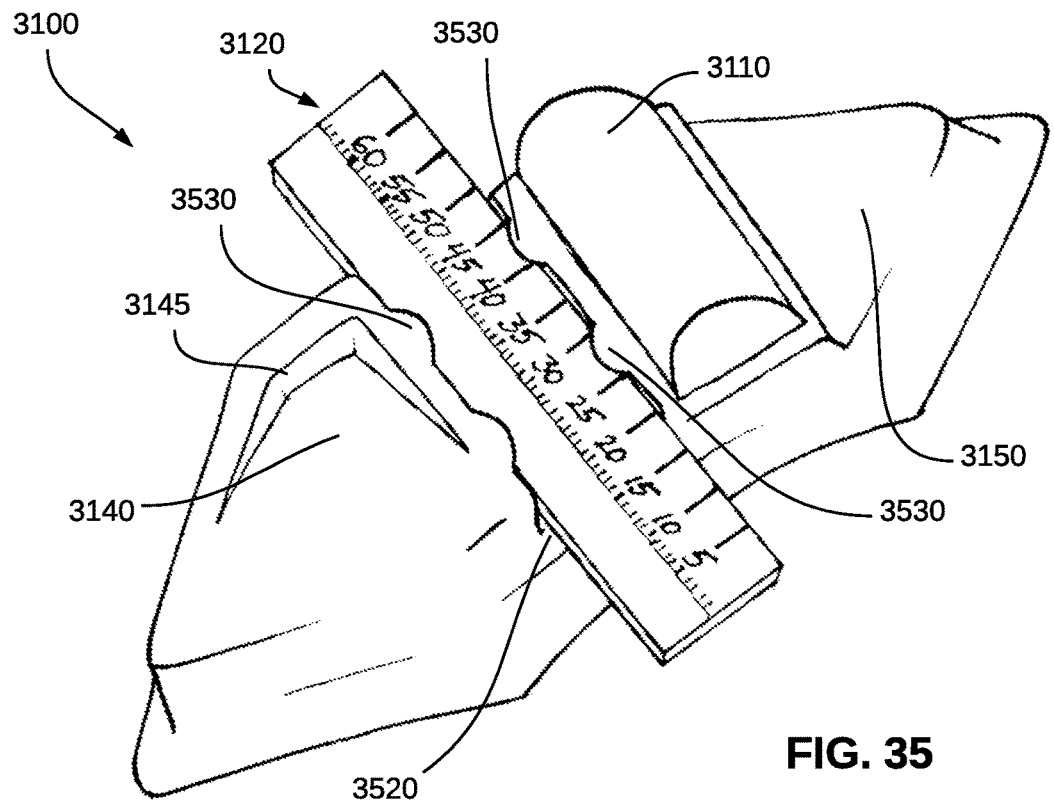
FIG. 35
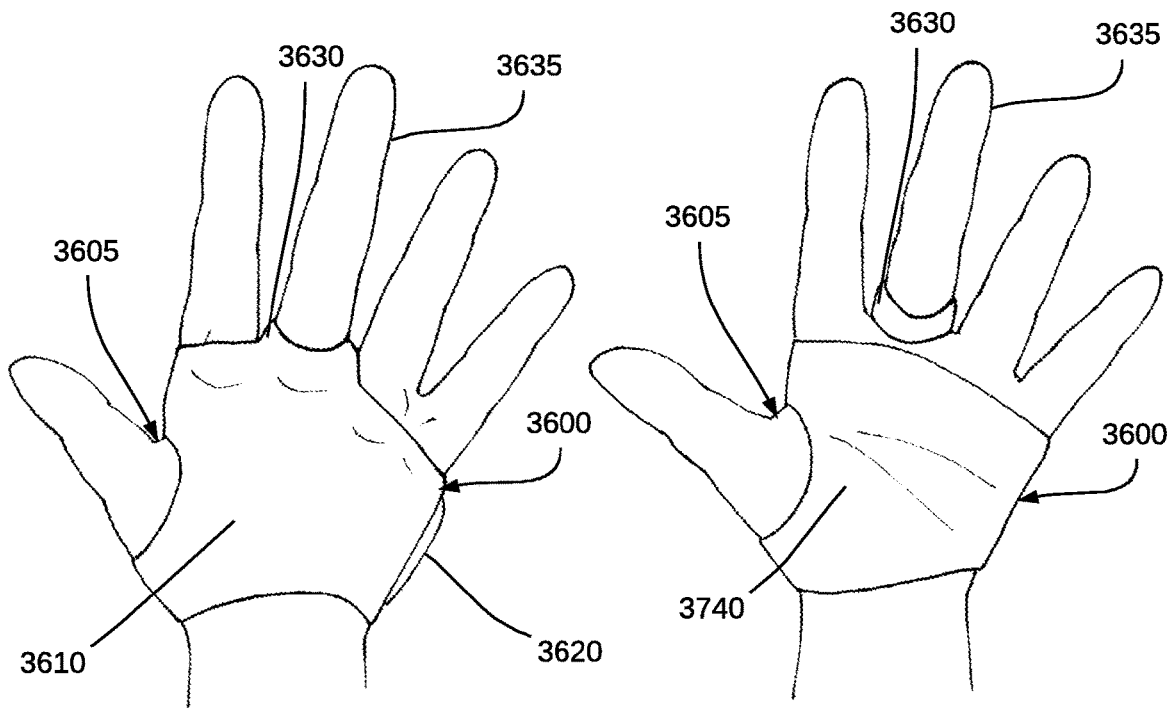
FIG. 36
FIG. 37

MODULAR WORKSPACE PLATFORM SYSTEM, ACCESSORIES THEREFOR, AND ASSOCIATED METHODS

PRIORITY CLAIM

The present application claims the benefit of U.S. Provisional Patent Application Ser. No. 62/804,725, filed Feb. 12, 2019 and entitled "Modular Workspace Platform System, Accessories Therefor, and Associated Methods," which application is incorporated herein by reference in its entirety.

FIELD OF THE INVENTION

The present invention relates to utility straps and, more specifically, modular and configurable systems of accessories for making small tools more accessible during manual procedures.

BACKGROUND OF THE INVENTION

Many professions requiring manual dexterity often call for the assistance of additional hands because two hands are simply not enough for certain procedures. Additionally, the lack of a convenient work surface at or near the location, at which the procedures are being administered, can lead to mistakes such as dropped tools and materials.

One example of such a profession is dentistry, in which a dentist and an assistant frequently work together using 4-handed dentistry techniques to treat patients in a choreographed way. For example, often times several dental instruments, products, and devices are transferred between a distant work surface and four hands in and around a patient's oral cavity. The material transfer between the dentist and the assistant can lead to a variety of problems including:

1. Loss of time during the transfer process of the materials;
2. Inefficiencies in manipulating and adjusting multiple items;
3. Reduction in field of vision of the oral cavity due to hands and items repeatedly entering and exiting the oral cavity;
4. Increased chances for error, such as dropped instruments and wrong items being passed to the dentist;
5. Prolonged treatment procedures due to procedural errors;
6. Waste of dental products and supplies;
7. Short and long-term health risks associated with eye strain and musculo-skeletal postural complications associated with fatigue, strain, and poor ergonomics; and
8. Decreased quality in procedures and patient care, thus leading to higher rates of patient dissatisfaction.

Thus far, these problems have only been addressed by the addition of assistants, modifications to dental furniture, work space, work surface, dental chair, and procedural systems. While a limited number of devices attaching to individual fingers, such as rings for inserting containers of pre-measured prophy paste, offer some remedy, many of these devices require finger manipulation, thereby inhibiting free movement of the fingers. Other devices use molded shapes to accommodate dental materials but do not allow attachment to a convenient surface nor offer the necessary stability and rigidity for ergonomic use. There is a need for solutions to assist those in highly manual professions in performing complicated tasks.

SUMMARY OF THE INVENTION

In accordance with the embodiments described herein, a modular workspace platform system for providing a mobile work surface for a user includes a workspace platform attachable to a location specified by the user. The workspace platform includes a compact work surface for use in performing at least one manual task including temporarily storing a material, mixing two or more materials, temporarily supporting a tool, and providing a tool cleaning surface.

In an embodiment, the compact work surface includes at least one of a trough, a tapered channel, a tool insertion slot, a wipe holder, a textured surface configured as the tool cleaning surface, a mixing surface a ruler holder, an adhesive band, and a matrix ring holder. In a further embodiment, the trough is configured for containing at least one of a liquid, a gel, a powder, a foam, and a mechanical component. In an embodiment, the trough is trapezoidal in shape.

In still another embodiment, the modular workspace platform system is configured to be attachable to a backside of a hand. In an embodiment, the hand is covered by a glove, and the workspace platform is configured to be attachable to the glove.

In a further embodiment, the workspace platform is formed of a pliable material. In an alternative embodiment, the workspace platform conforms to a contour of an attachment location.

In another embodiment, the workspace platform also includes linear gradations. Alternatively, the workspace platform includes an adhesive for attaching to an attachment location. In an embodiment, the workspace platform is configured to be disposable. In an alternative embodiment, the workspace platform is configured to be reusable and, in a further embodiment, the workspace platform is configured to be compatible with sterilization procedures.

In yet another embodiment, the modular workspace platform includes a removable hand and/or arm strap for accommodating the workspace platform thereon. In an embodiment, the removable hand and/or arm strap is configured to be reusable and, in a further embodiment, the removable hand and/or arm strap is configured to be compatible with sterilization procedures.

In still another embodiment, the removable hand strap and the workspace platform include one of matingly engaging snaps, magnets, and hook-and-loop attachments for removably attaching the workspace platform onto the removable hand strap. In an embodiment, the removable hand strap is configured for accommodating hands of a variety of sizes.

In an embodiment, a method for performing dental procedures includes providing a modular workspace platform, attaching the modular workspace platform to a first hand, and, with a second hand, executing at least one manual task including mixing two or more materials, temporarily storing a tool, and cleaning the tool on the modular workspace platform while treating a first patient.

In a further embodiment, the method also includes removing the modular workspace platform from the first hand, sterilizing the modular workspace platform, and reusing the modular workspace platform in treating a second patient.

BRIEF DESCRIPTION OF THE DRAWINGS

FIG. 1 shows a top view of a modular workspace platform, in accordance with an embodiment.

FIGS. 2-4 show cross-sectional views of the modular workspace platform, such as that of FIG. 1, shown here to illustrate different options for attachment mechanisms.

FIGS. 24 and 25 show top and bottom views of a utility hand strap as worn on a hand, in accordance with an embodiment.

FIG. 26 shows an ISO view of an alternative utility hand strap as worn on a hand, in accordance with an embodiment.

FIG. 27 shows an ISO view of the utility hand strap of FIG. 26, shown here with a modular workspace platform attached thereto, in accordance with an embodiment.

FIGS. 28 and 29 show a bottom view of a modular workspace platform including adhesive features, in accordance with an embodiment.

FIGS. 30-35 show ISO views of variations of modular workspace platforms, in accordance with embodiments described herein.

FIGS. 36 and 37 show different views of still another utility hand strap including a rotation prevention feature, in accordance with an embodiment.

DETAILED DESCRIPTION OF EMBODIMENTS OF THE INVENTION

Figure 5:
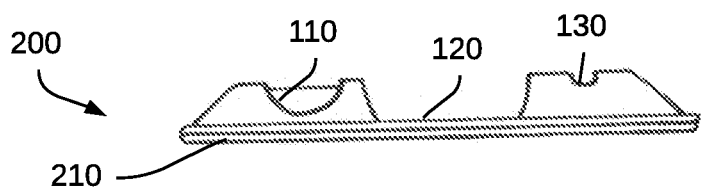
FIGS. 5-7 show cross-sectional views, from a perpendicular angle from FIGS. 2-4, of the modular workspace platform of FIG. 1.

The present invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In the drawings, the size and relative sizes of layers and regions may be exaggerated for clarity. Like numbers refer to like elements throughout.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items, and may be abbreviated as "/".

It will be understood that when an element or layer is referred to as being "on," "connected to," "coupled to," or "adjacent to" another element or layer, it can be directly on, connected, coupled, or adjacent to the other element or layer, or intervening elements or layers may be present. In contrast, when an element is referred to as being "directly on," "directly connected to," "directly coupled to," or "immediately adjacent to" another element or layer, there are no intervening elements or layers present. Likewise, when light is received or provided "from" one element, it can be received or provided directly from that element or from an intervening element. On the other hand, when light is received or provided "directly from" one element, there are no intervening elements present.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. Accordingly, the regions illustrated in the figures are schematic in nature and their shapes are not intended to illustrate the actual shape of a region of a device and are not intended to limit the scope of the invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

As described in the present disclosure, a modular workspace platform system provides a flexible, mobile work surface for a user. The modular workspace platform system includes a workspace platform that is attachable to a user's hand or a specialized utility hand strap. The workspace platform includes one or more features such as, but not limited to, containment forms, adhesive strips, mixing troughs, gauze holder, retention features, a flat work surface, and other structures that are useful for specific applications. Different combinations of these features can be included in the workspace platform such that the workspace platform can be used in a variety of applications such as different areas of dentistry (general, hygiene, restorative, cosmetic, endodontics, orthodontics, periodontics, implantology, etc.), cosmetology, hobbies and crafts, and for other tasks. The workspace platform is attachable in a variety of positions and configurations, depending on user preference with tasks and procedures. Workspace platform can be formed of materials that are suitable for disposal after a single use, or alternatively can be formed of a material compatible with cleaning and sterilization procedures such that the workspace platform can be, for example, autoclaved and reused. Additionally, the material used to form the workspace platform should be chemically resistant to the chemicals used with a particular application. For example, for dental applications, the material should be resistant to commonly used dental chemicals, such as epoxies and amalgams.

In an example, the workspace platform is formed of a rigid material, or can be formed of a flexible or pliable material that conforms to the attachment location, such as the back of a hand. A variety of thicknesses, configurations, and design features are contemplated in order to accommodate the needs of a specific application and user preference. Different mechanisms, such as snaps, magnets, adhesives, and hook-and-loop attachments, are contemplated for attachment to the attachment location, such as the back of a hand or other locations that is convenient for the user for a specific application. Multiple workspace platforms can be used simultaneously by a single user or multiple cooperating users working together on a task.

Turning now to the figures, FIG. 1 shows a workspace platform 100, in accordance with an embodiment. Workspace platform 100 includes a plurality of features, such as wells 110, a flat work surface 120, and a channel 130. Additionally, a first opening 150 under a first section 152, which contains wells 110, and a second opening 160 under a second section 162, which contains channel 130, can serve to accommodate, for instance, a stack of sponge gauze, blotting paper, cotton pads, or other components therein. As shown in FIG. 1, wells 110 are circular indentations suitable for containing, for example, chemicals, pastes, epoxies, and even small mechanical components, such as brackets and screws. Shapes other than circular indentations are contemplated for wells 110, as will be described at an appropriate juncture hereinafter. Flat work surface 120 is suitable for, for example, mixing small amounts of epoxies or other materials thereon. Also, channel 130 is configured to accommodate standard tools of a particular application, such as a dental microbrush, therein as a tool holder. In the illustrated exemplary embodiment, workspace platform 100 tapers to rounded triangular points 142 at the sides so as to fit onto the back of a user's hand, for instance. Other shapes, such as rounded or square sides, are also contemplated to accommodate different applications of workspace platform 100. Also, while workspace 100 is shown to be left-right and top-bottom symmetric in overall shape, asymmetric configurations are also contemplated. For example, as shown, workspace 100 can be rotated according to user preference such that troughs 110 are located to the left of channel 130, or vice versa. Alternatively, the workspace can be formed asymmetrically, for instance, specifically for placement on the right or the left hand.

Workspace platform 100 is configured for attachment to a location specified by the user. Some suitable locations are, for example, the back of the non-dominant hand of the user such that the user can perform procedures for, for example, dentistry with the dominant hand, such as mixing two or more materials, temporarily storing a tool, and cleaning the tool on the workspace platform. Workspace platform 100 also provides an additional benefit of protecting the attachment location from irritants and friction. For example, dentists often use the back or the side of the gloved non-dominant hand as a convenient place to wipe tools or to mix small amounts of materials, and make-up artists use the back or the side of the non-dominant hand to mix make-up colors and wipe brushes, both of which can lead to skin irritation, contact dermatitis, and other problems. By using workspace platform to cover and protect the attachment location, such problems can be avoided while providing additional functionality to assist with the tasks at hand.

FIGS. 2-7 are cross-sectional views of different variations of workspace platform 100, shown here to illustrate different attachment mechanisms for attaching workspace platform 100 to a location specified by the user. For instance, FIG. 2 shows a workspace platform 200 including an adhesive layer 210. Adhesive layer 210, when exposed, can be used to attach workspace platform 200 to, for instance, the back of the hand of the user or an assistant, to the patient chair or bib, or another convenient surface.

Figure 6:
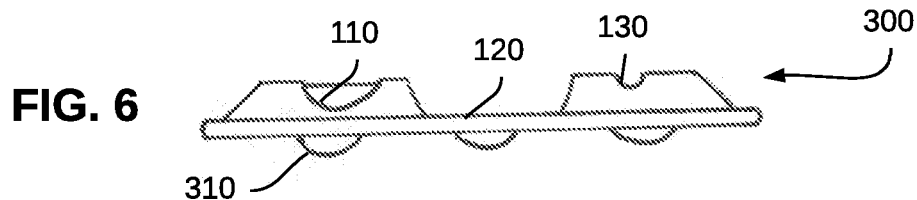
Figure 7:
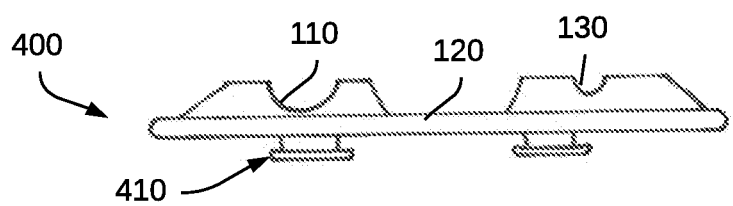

FIG. 3 shows a workspace platform 300 including a plurality of magnetic components 310, shown here as spherical segments, that are attachable via magnetic forces to another surface including complementary magnetic features therein. Similarly, FIG. 4 shows a workspace platform 400 including a plurality of snap mechanisms 410, including stand-offs 412 and lip features 414, which matingly engage complementary features on another surface, as will be described hereinafter. FIGS. 5-7 show cross-sectional views as seen from a perpendicular viewing angle from FIGS. 2-4, respectively.

Figure 8:
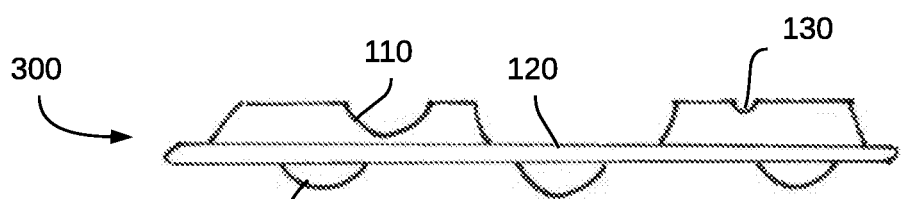
FIG. 8 shows a magnetic attachment arrangement for use with the attachment mechanism shown in FIGS. 3 and 6, in accordance with an embodiment.
Figure 9:
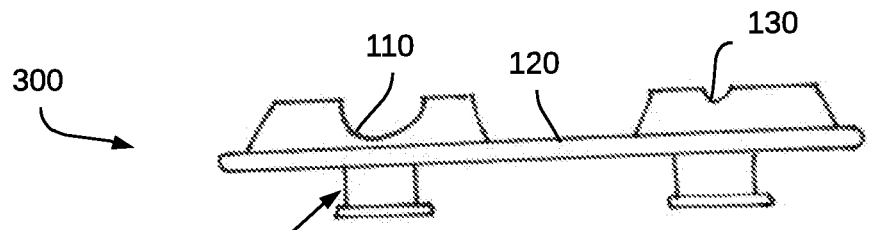
FIG. 9 shows a button-and-loop attachment arrangement for use with the attachment mechanism shown in FIGS. 4 and 7, in accordance with an embodiment.

FIGS. 8 and 9 illustrate different mechanisms by which workspace platform can be attached to another surface including complementary attachment mechanisms. For example, FIG. 8 shows a surface 800 including a plurality of indentations 810, each one of the indentations being located over one of a plurality of magnets 812 embedded within surface 800. Plurality of indentations 810 and magnets 812 are configured to be complementary to magnetic components 310 of workspace platform 300 such that workspace platform 300 is attachable to surface 800 via magnetic forces. Similarly, FIG. 9 shows a surface 900 including a plurality of openings 910, each one of the plurality of openings 910 including a wall 912 and a notch feature 914 formed into wall 912 and complementary to standoffs 412 and lip features 414 of workspace platform 400 such that workspace platform 400 is attachable to surface 900 by clipping snap mechanisms 410 into openings 910. Surfaces 800 and 900 may be formed, in an example, as part of an external strap or other device, such as a hand strap, wrist strap, or a mat attachable to another surface, which is suitable for serving as an attachment location for an embodiment of the workspace platforms described herein.

Figure 10:
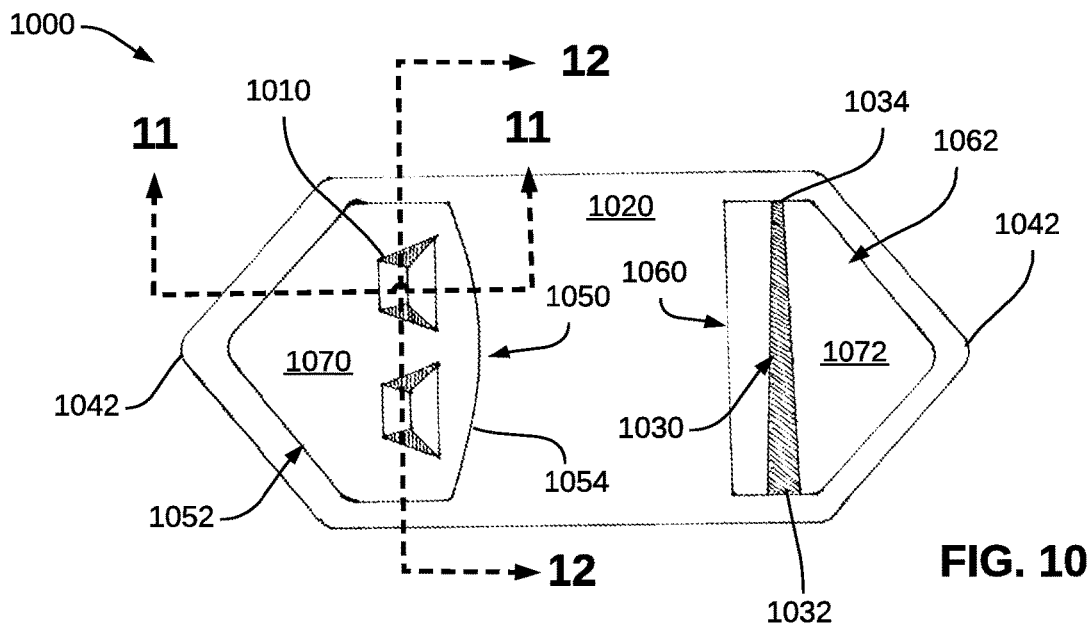
FIG. 10 shows a top view of another modular workspace platform, in accordance with an embodiment.
Figure 11:
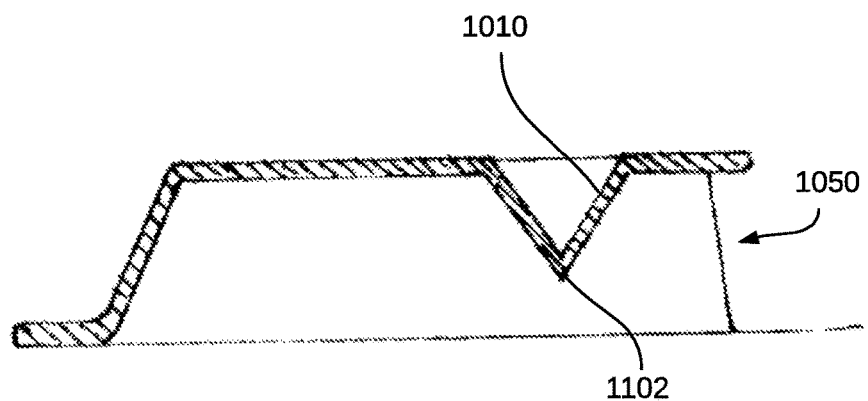
FIG. 11 shows a cross-sectional view of the modular workspace platform of FIG. 10, shown here to illustrate the shape of the trapezoidal troughs, in accordance with an embodiment.
Figure 12:
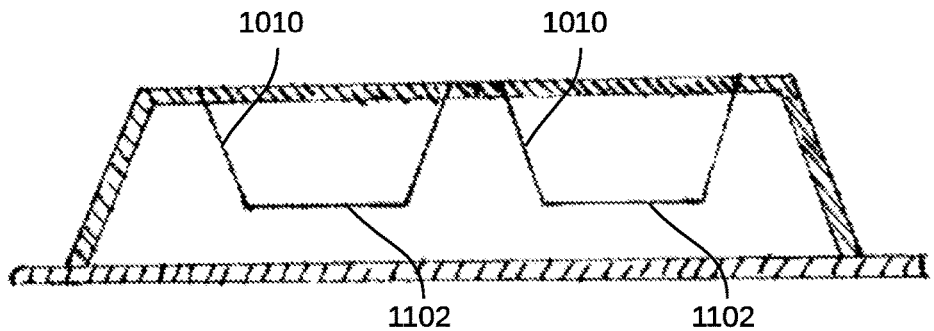
FIG. 12 shows a cross-sectional view, from a perpendicular angle from FIG. 11, of the modular workspace platform of FIG. 10, shown here to further illustrate the shape of the trapezoidal troughs, in accordance with an embodiment.

FIGS. 10-12 illustrate another embodiment of a workspace platform 1000. Referring first to FIG. 10, workspace platform 1000 includes trapezoidal troughs 1010, a flat work surface 1020, and a tapered channel 1030. In particular, tapered channel 1030 is configured with a narrowing taper from a wide end 1032 to a narrow end 1034. Thus, when a thin tool (not shown in FIG. 10), such as a dental microbrush, is inserted into tapered channel 1030, the thin tool is securely wedged and held by narrow end 1034. In this way, tapered channel 1030 is able to securely hold in place tools and components of a variety of shapes and diameters therein. Workspace platform 1000 is also symmetrically tapered at the sides into rounded triangular points 1042. As previously discussed, the workspace platform can also be shaped asymmetrically for placement specifically on the left or right hand, for example. Furthermore, a first opening 1050 in a first section 1052, including a rounded lip feature 1054, and a second opening 1060 in a second section 1062 can serve to hold a stack of sponge gauze, blotting paper, cotton pads, and the like therein. Still further, a first flat surface 1070 and a second flat surface 1072 can also serve as work surfaces on which tasks such as mixing of chemical components and wiping off of tools can be performed.

Further details of trapezoidal troughs 1010 are illustrated in FIGS. 11 and 12. A partial cross-sectional view of workspace platform 1000 through one of troughs 1010 is shown in FIG. 11. In this view, it can be seen that a bottom 1102 of trough 1010 tapers to a point in this cross-sectional view. In the view shown in FIG. 12, which illustrates a cross-sectional view of workspace platform 1000 along the bottom of trough 1010 along a line perpendicular to the cross-sectional line taken in FIG. 11, it can be seen that bottom 1102 of trough 1010 tapers to a ridge. In such a trapezoidal design with a tapered bottom 1102, a liquid, gel, or other material placed within trough 1010 is collected along the ridge of trough 1010 such that the material within trough 1010 does not as quickly evaporate or harden as it would had the material been placed in a well with a flat or spherical bottom. In addition, tapered bottom 1102 serves as a retention feature for components, such as a stack of sponge gauze, inserted into first opening 1050. Rounded lip feature 1054 also serves as a retention feature when components inserted into first opening 1050 are removed therefrom.

Figure 13:
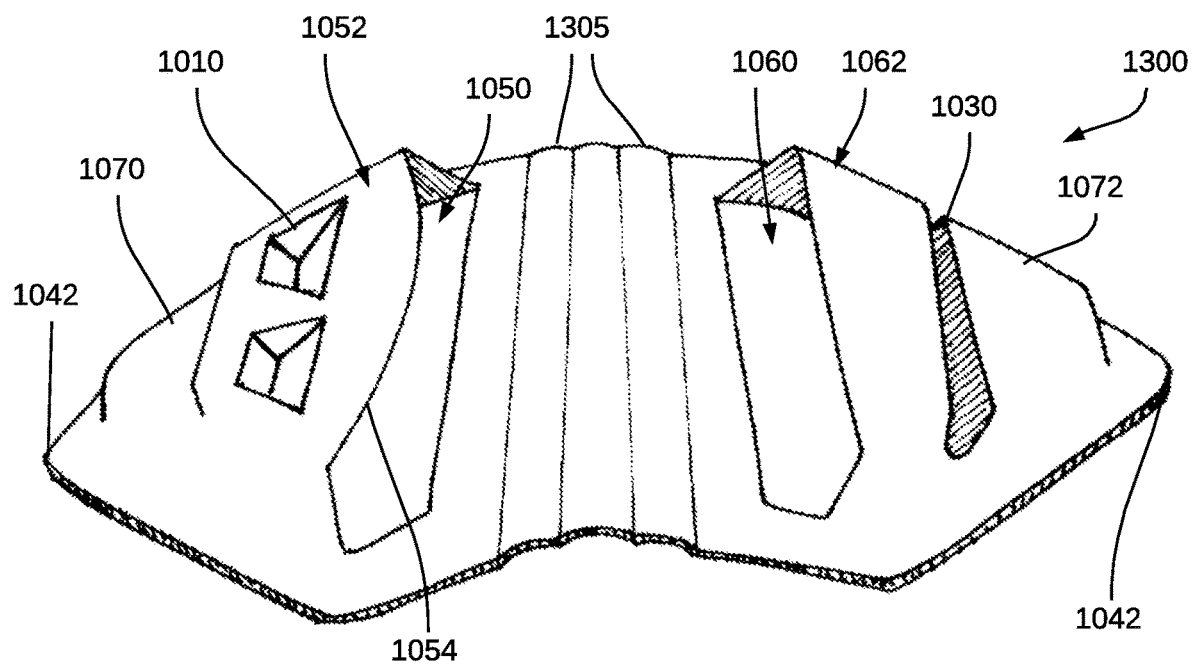
FIG. 13 shows an ISO view, in elevation, of still another modular workspace platform including trapezoidal troughs, in accordance with an embodiment.

Turning now to FIG. 13, a variation of workspace platform 1000 of FIG. 10 is shown. FIG. 13 shows a workspace platform 1300, which includes a plurality of creased sections 1305. Creased sections 1305 enable workspace platform 1300 to flexibly conform to an attachment location, such as the back of a hand, even if workspace platform 1300 is formed of a relatively rigid material, such as a firm plastic compatible with cleaning and sterilization processes.

Figure 14:
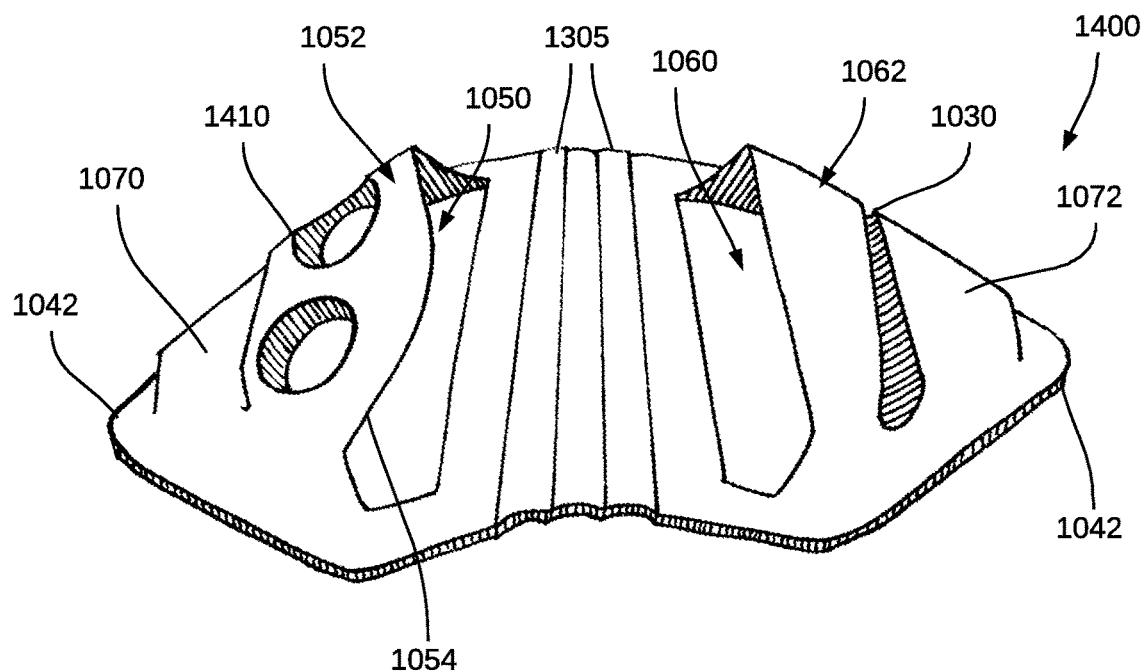
FIG. 14 shows an ISO view, in elevation, of yet another modular workspace platform including circular wells, in accordance with an embodiment.

Another variation of workspace platform 1300 is shown in FIG. 14. A workspace platform 1400 is similar to workspace platform 1000 of FIG. 10 and workspace platform 1300 of FIG. 13, although workspace platform 1400 includes two circular wells 1410 rather than the trapezoidal troughs used in workspace platforms 1000 and 1300. For certain applications, such as those requiring the use of relatively large amounts of pastes or mechanical components, such circular wells can be preferable over the trapezoidal troughs.

Figure 15:
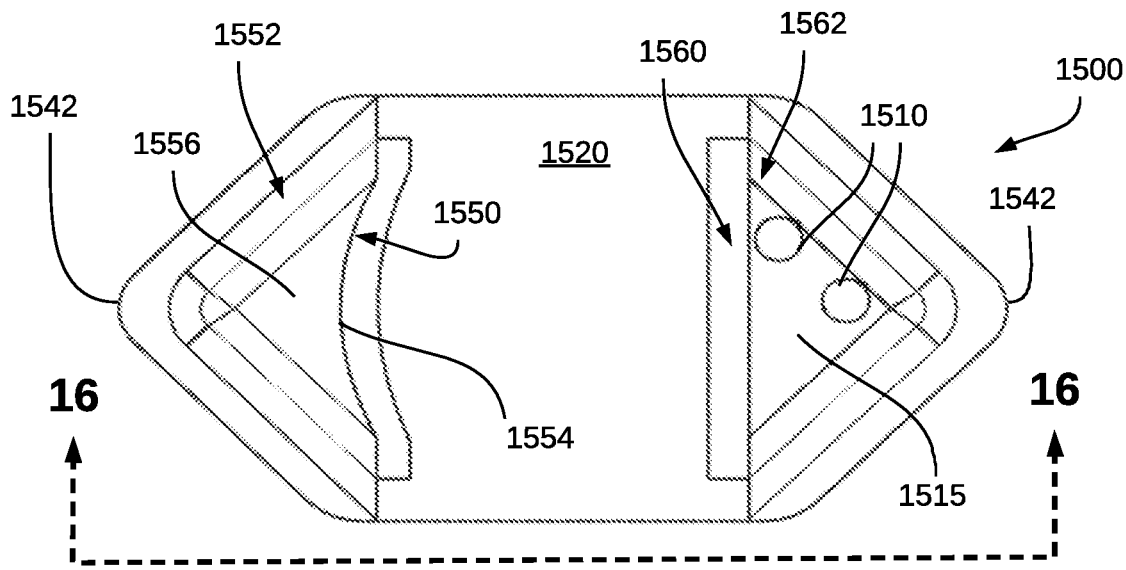
FIGS. 15 and 16 show top and side views, respectively, of yet another modular workspace platform, in accordance with an embodiment.

FIGS. 15-18 illustrate another exemplary embodiment of a workspace platform. As shown in FIG. 15, a workspace platform 1500 includes circular wells 1510 positioned such that a small, first work surface 1515 is located immediately adjacent to circular wells 1510. A larger, second work surface 1520 is located in a middle section of workspace platform 1500, which tapers at the edges to rounded triangular points 1542. Workspace platform 1500 further includes a first opening 1550 in a first section 1552. First section 1552 also includes a concave lip feature 1554, which can be more desirable for certain types of components insertable into first opening 1550. A top area of first section 1552 serves as a third work surface 1556. Additionally, a second opening 1560 is located in a second section 1562, which also includes circular wells 1510 and first work surface 1515 therein.

Figure 16:
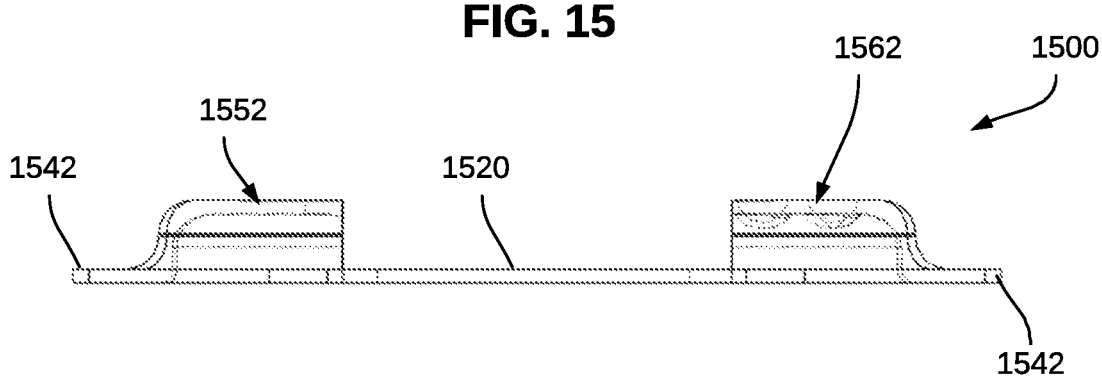
Figure 17:
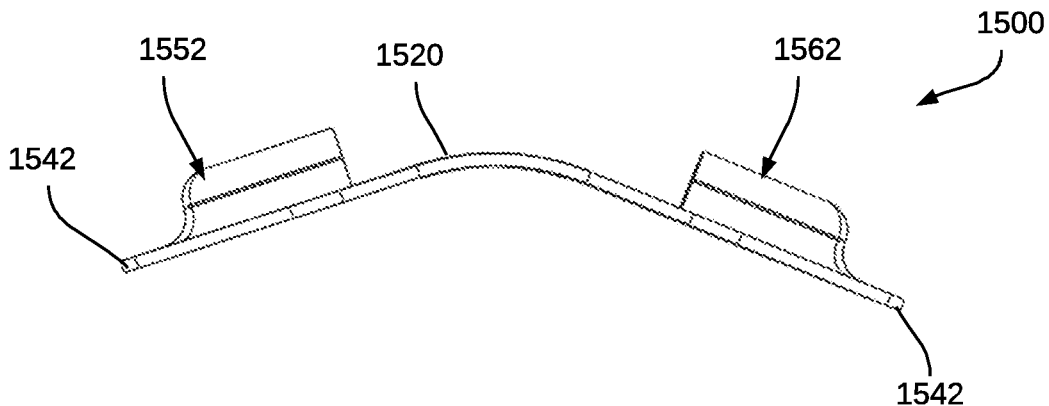
FIG. 17 shows a side view of the modular workspace platform of FIGS. 15 and 16, shown here to illustrate a flexed configuration, in accordance with an embodiment.
Figure 18:
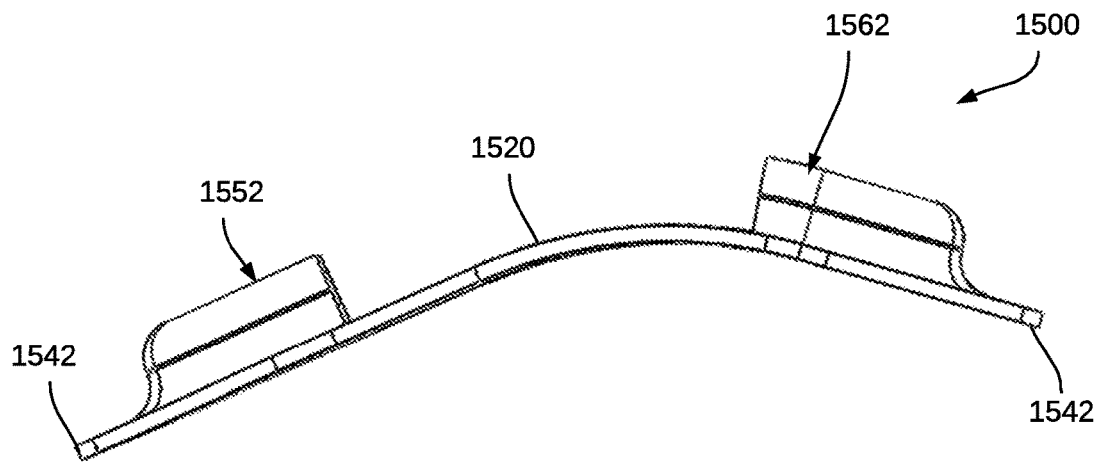
FIG. 18 shows a side view of the modular workspace platform of FIGS. 15 and 16, shown here to illustrate an asymmetric flex configuration, in accordance with an embodiment.

A side view of workspace platform 1500 is shown in FIG. 16. As visible in FIG. 16, workspace platform 1500 is flat across the bottom, and can be formed of, for instance, a relatively firm plastic for stability. With the selection of an appropriate material to form workspace platform 1500, second work surface 1520 can be configured to be pliable so as to bend to conform to the shape of the attachment location, as shown in FIG. 17, even without the inclusion of creased sections, as were shown in FIGS. 13 and 14. Further, if a large enough area is dedicated to second work surface 1520 and the appropriate pliable material is chosen, second work surface 1520 can even bend asymmetrically, as shown in FIG. 18.

Figure 19:
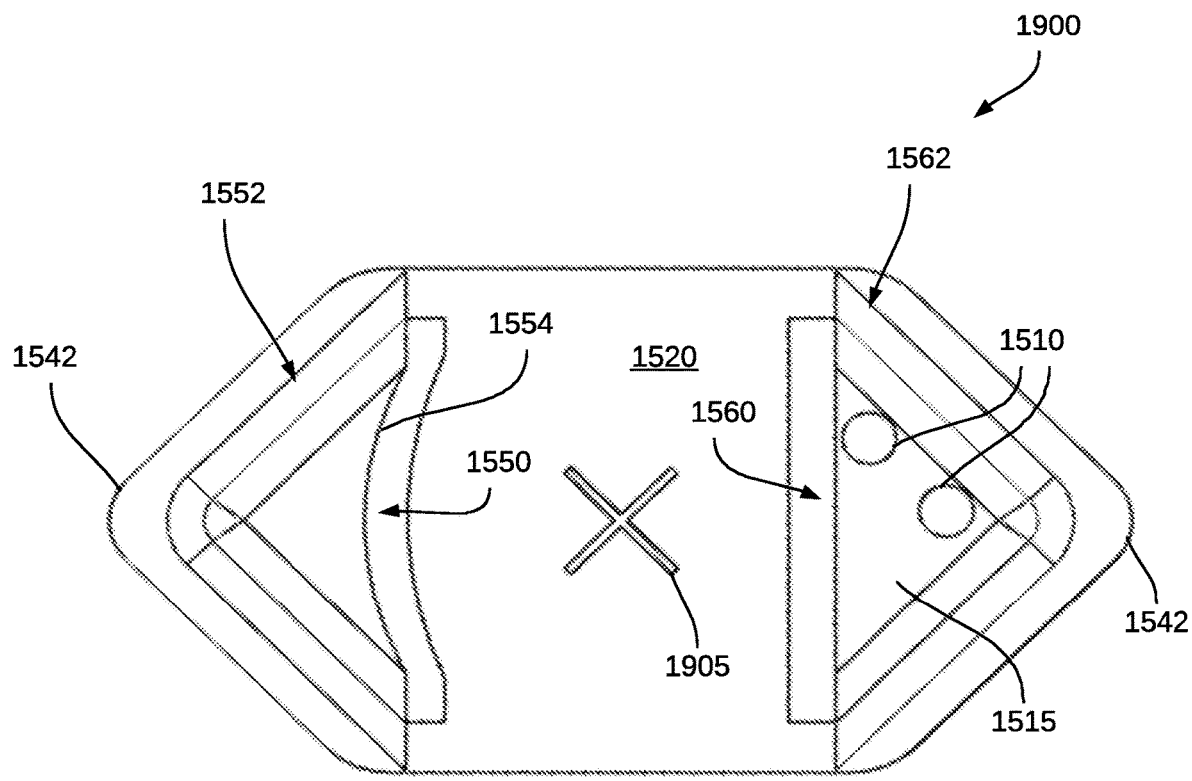
FIG. 19 shows a modular workspace platform including a retention feature, in accordance with an embodiment.

FIG. 19 shows a top view of a variation of workspace platform 1500. In addition to the components of workspace platform 1500, a workspace platform 1900 includes a retention feature 1905, which is an x-shaped opening cut into second work surface 1520. Retention feature 1905 can be used to hold a component of various sizes and shapes therein. For example, a piece of gauze can be inserted into retention feature 1905, or even mechanical components such as spacers, wedges, screws, pins, and other small implements used in specific applications, such that these components are removably held by retention feature 1905.

Figure 20:
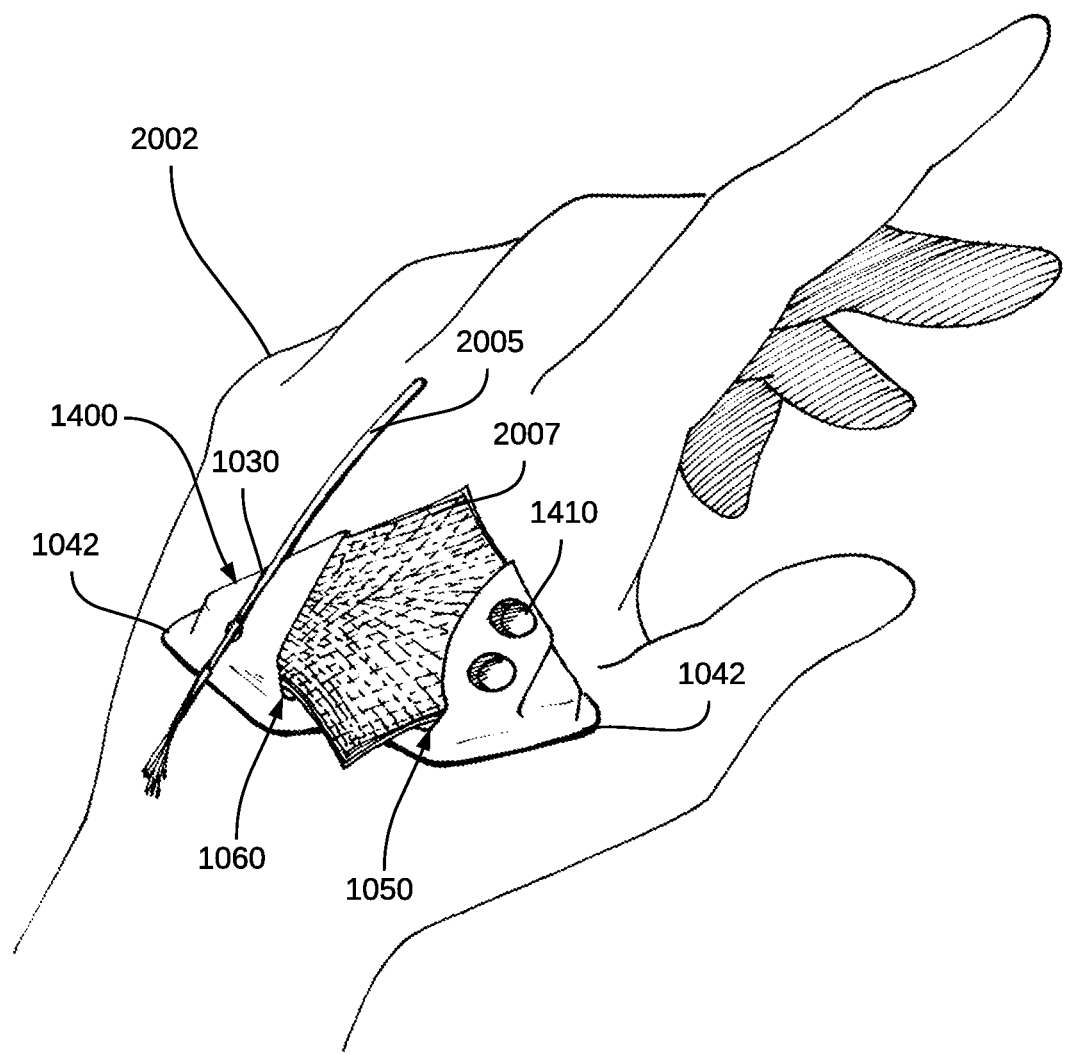
FIG. 20 shows a modular workspace platform, including a stack of gauze inserted into a gauze dispenser arrangement and a microtool held in a tool slot, as attached to the back of a hand, in accordance with an embodiment.

FIG. 20 shows workspace platform 1400 of FIG. 14 as attached to the back of a left hand 2002, in accordance with an embodiment. As shown in FIG. 20, a microbrush 2005 is inserted into tapered channel 1030, and a stack of gauze 2007 is held in first opening 1050 and second opening 1060. Workspace platform 1400 is attached to left hand 2002 using, for example, an adhesive. Workspace platform 1400 conforms to the curvature of the back of left hand 2002, and can be attached directly to the back of left hand 2002 for certain non-sterile applications, or attached to a glove surface covering left hand 2002 for applications requiring gloves and maintenance of sterility of components.

Figure 21:
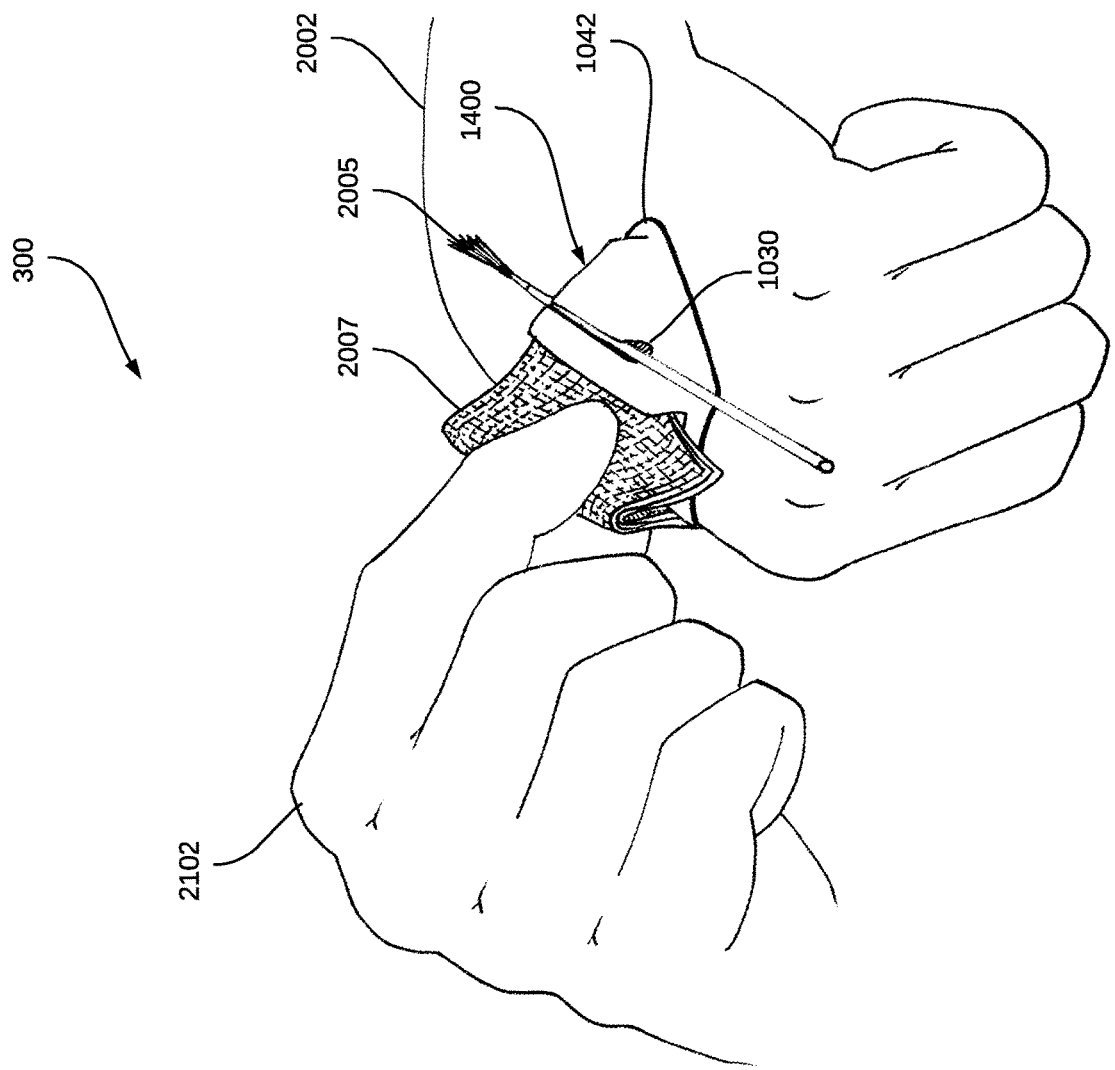
FIG. 21 illustrates a manner in which gauze is removed from or inserted into the gauze dispenser arrangement of the embodiments illustrated in FIG. 20.

FIG. 21 illustrates a manner in which gauze 2007 is removed by a right hand 2102 while workspace platform 1400 is attached to the back of left hand 2002. It is noted that workspace platform 1400 (and other embodiments of the workspace platform described herein) can be positioned in a variety of orientations in accordance with user preference, including on the back of the right hand as well as on other surfaces such as a patient bib and a tool tray.

Figure 22:
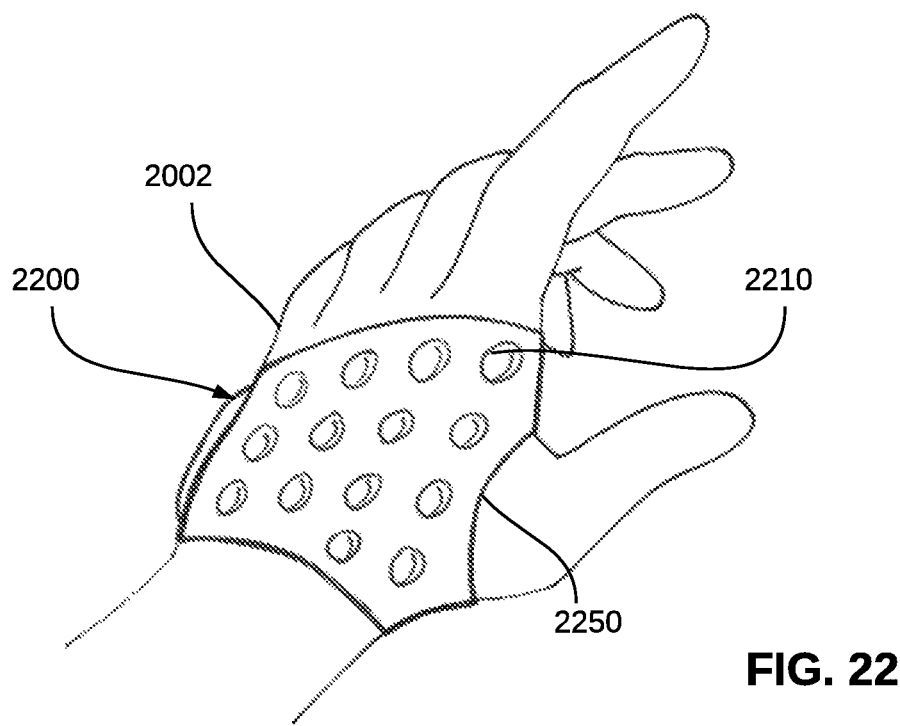
FIG. 22 shows an ISO view of a utility hand strap as worn on a hand, in accordance with an embodiment.

FIG. 22 shows an ISO view of a utility hand strap for use with a workspace platform, in accordance with an embodiment. In an example, a utility hand strap wraps around the hand and includes coverage of the back of the hand, between the thumb and index finger and below the thumb area, across the palm and over the lateral side. As shown in the described examples, a utility hand strap does not cover the fingers, thus allowing full mobility and range of motion of all fingers and thumb. In the embodiments illustrated below, the utility hand strap acts as the base onto which one or more workspace platform can be attached and supported in desired positions and configurations. Anatomically, in a pronated position, the utility hand strap wraps around the dorsal hand from the lateral area covering the hypothenar muscles, extending over the metacarpals, superior to the phalanges, inferior to the carpals, continuing medially across both the thenar and interosseous muscles. The utility hand strap extends over the ventral hand from interosseous and polici muscles, inferior to the flexor retinaculum and superior to the attachment of lumbrical muscles, across the abductor digiti minimi muscles, and terminating back around the hypethenar muscles.

As shown in FIG. 22, a utility hand strap 2200 includes a plurality of attachment features 2210 therein, as well as a thumb hole 2250, such that utility hand strap 2200 can be strapped on around left hand 2002 without impeding the movement of the fingers. Attachment features 2210 can be, for example, indentations 810 (with embedded magnets) as shown in FIG. 8 or openings 910 as shown in FIG. 9. Other attachment features, such as male-to-female insertion mechanisms and combinations of magnetic, adhesive, or other fastening components, can be used to attach the utility hand strap to the user's hand and to attach the modular workspace platform components.

Figure 23:
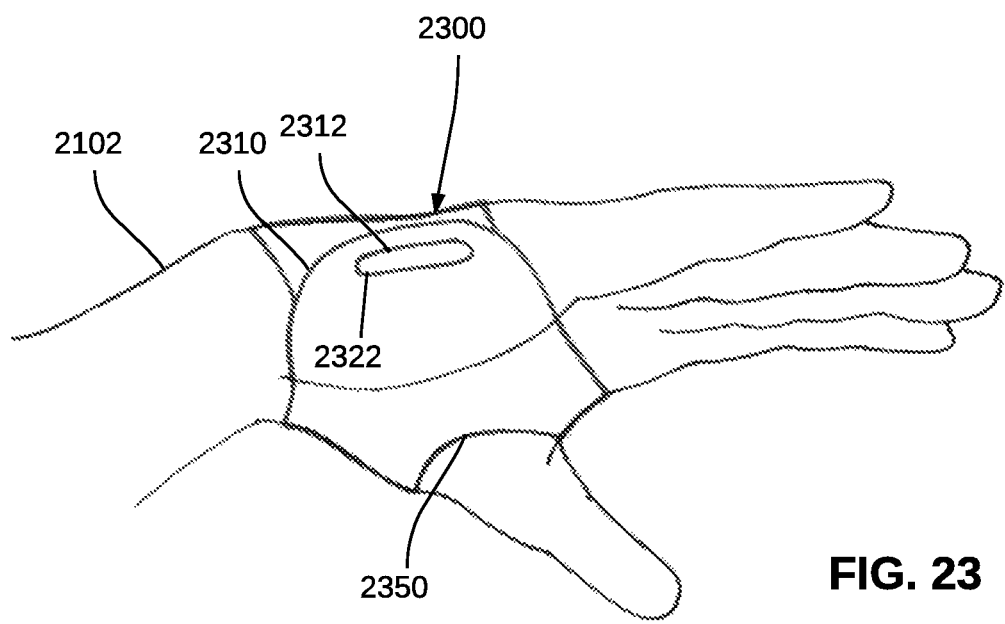
FIG. 23 shows a side view of a utility hand strap as worn on a hand, in accordance with an embodiment.

With the selection of an appropriately pliable material, such as an FDA-approved silicone or a combination of synthetic materials, to form utility hand strap 2200, utility hand strap 2200 can be used ambidextrously. For example, while utility hand strap 2200 is shown in FIG. 22 as worn on a left hand, if formed of a pliable material, utility hand strap 2200 can be flipped inside-out and worn on the right hand, as shown in FIG. 23. Also, if a flexible, sterilizable material, such as polypropylene or another autoclave-compatible material (i.e., can withstand autoclave temperatures such as 132° C. and higher) or a material that can be chemically disinfected is chosen, then utility hand strap 2200 can be sterilized and repeatedly reused. For instance, the utility hand strap can be formed of an FDA-approved silicone, which is elastomeric, flexible, form-fitting, lightweight, and 2 to 8 millimeters in overall thickness. As an example, the utility hand strap can be configured to be worn over thin polymer (e.g., nitrile or latex) gloves, when working directly with patients, and is reusable after sterilizing or disinfecting. When not working directly with patients, the hand strap can be worn without gloves.

In an exemplary embodiment, the utility hand strap is a fingerless strap that wraps around a user's hand in adjustable and form-fitting way, formed of an FDA-approved elastomeric material that is sterilizable or can be disinfected using by thermal and/or chemical methods, and is reusable. The utility hand strap can also be contoured, perforated (for attachment of workplace platforms thereon and/or ventilation), and flexible for comfort. The utility hand strap is configured for attaching one or more workspace platform components thereon.

FIG. 23 shows a side view of a utility hand strap 2300 as form on right hand 2102. Utility hand strap 2300 includes a flap 2310 including an opening 2312 configured for accommodating an elongated tab 2322 therein, thus securing utility hand strap 2300 around right hand 2102 with the thumb accommodated through a thumb hole 2350. Alternatively, opening 2312 and elongated tab 2322 can be replaced with another fastening mechanism such as, but not limited to, hook-and-loop (e.g., VELCRO® fasteners for non-sterile applications), buttons, snaps, magnets, and hooks. The fastening mechanism can be adjustable such that the utility hand strap can fit firmly or loosely around the hand.

FIG. 24 shows utility hand strap 2200 worn on left hand 2002, as seen from the palm side. As shown in FIG. 24, utility hand strap 2200 includes attachment features 2210 also on the palm side. FIG. 25 shows utility hand strap 2300 worn on right hand 2102, as seen from the back of the hand.

FIG. 26 shows an alternative embodiment of a utility hand strap 2600, which includes a flap 2610 and a thumb hole 2650 as in previous embodiments. As shown in FIG. 26, utility hand strap 2600 does not include attachment features and simply provides a flat surface 2660 onto which a workplace platform can be attached using, for instance, an adhesive.

FIG. 27 shows utility hand strap 2600 with a workspace platform 2700 attached thereto. Like previously discussed workspace platform embodiments, workspace platform 2700 includes two circular wells 2710 and a flat surface 2720. The sides of workspace platform 2700 taper to rounded triangular points 2742, which are configured to fit within an area of left hand 2002 between the index finger and the thumb, for example. Workspace platform 2700 also includes a first opening 2750 in a first section 2752, and a second opening 2760 in a second section 2762 such that other components, such as a stack of gauze, can be accommodated therein for ready access.

FIGS. 28 and 29 illustrate an exemplary embodiment of an adhesive arrangement for attaching a workspace platform onto an attachment location. FIG. 28 shows a bottom view of a workspace platform 2800, which combines features of previously discussed workspace platform examples. Workspace platform 2800 includes first and second openings 2801 and 2803, respectively, into which components, such as a stack of gauze, can be accommodated. Workspace platform 2800 also includes a rounded retention feature 2805 to aid in the dispensing of the components held within first and second openings 2801 and 2803. Ends of workspace platform 2800 taper to rounded triangular points 2842, similarly to previously discussed workspace platform examples.

Continuing to refer to FIG. 28 in conjunction with FIG. 29, workspace platform 2800 also includes an adhesive backing 2850, which covers an adhesive 2900 until a user is ready to attach workspace platform 2800 to a desired attachment location. Adhesive backing 2850 includes a tab 2852, which assists the user in removing adhesive backing 2850 from workspace platform 2800, thus exposing adhesive 2900. Examples of suitable materials for use as adhesive 2900 include, but are not limited to, polystyrene, polycarbonate, acrylics, silicone rubber, polyethylene, polypropylene, and synthetic rubbers.

Figure 30:
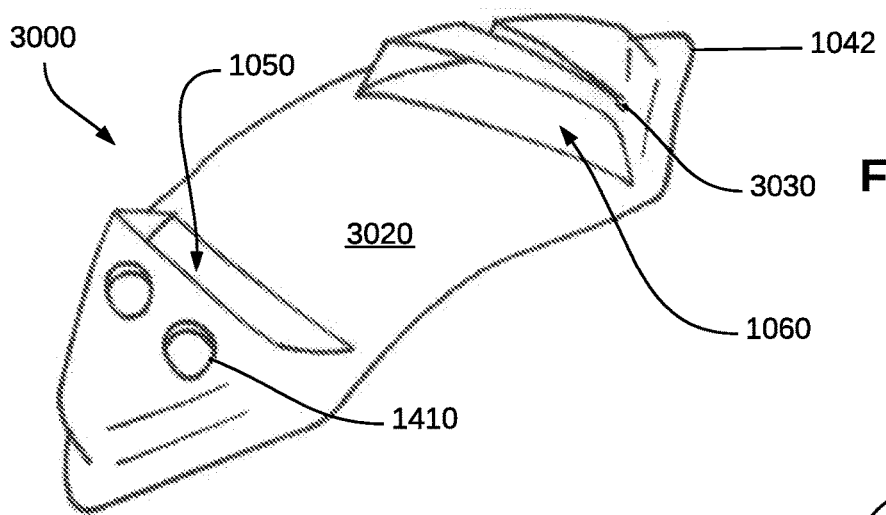

FIGS. 30-34 show ISO views of variations of workspace platforms, in accordance with embodiments described herein. As shown in FIG. 30, a workspace platform 3000 is a variation of workspace platform 1400 of FIG. 14, including a flat work surface 3020 instead of the creased sections, and the taper direction of tapered channel 3030 is reversed from that of tapered channel 1030 of FIG. 4. Workspace platform 3000 is useful, for example, in restorative/hygiene dentistry applications.

Figure 31:
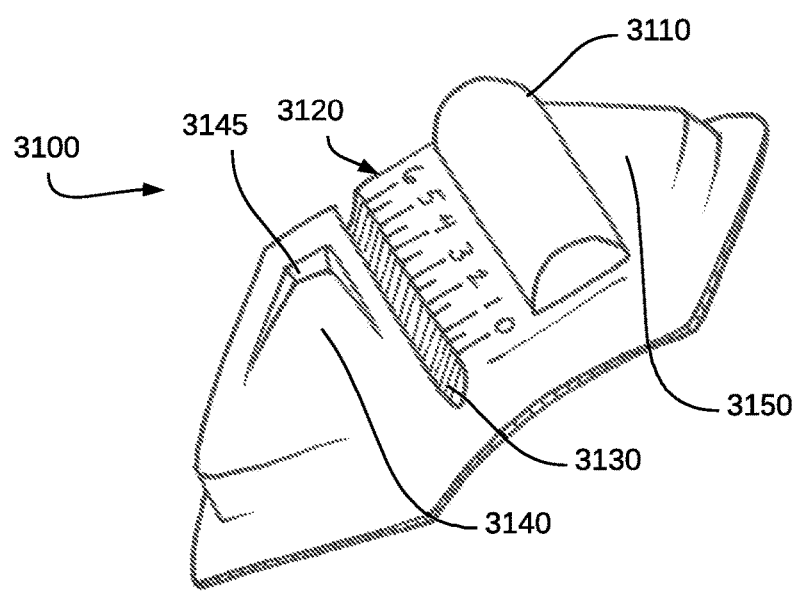

FIG. 31 shows a workspace platform 3100 including features that are useful for endodontics applications, in accordance with an embodiment. As shown in FIG. 31, workspace platform 3100 includes a raised, wiping surface 3110, a set of graduations (i.e., ruler marks) 3120, a slot 3130 for inserting components to be measured using graduations 3120, and an indented, flat mixing surface 3140 with retaining walls 3145 for containing less viscous liquids therein. An additional flat surface 3150 can be used as a flexible workspace such as for wiping tools and/or mixing viscous materials. Wiping surface 3110 can be smooth, as shown, or have a texture for aiding with the removal of materials from implements wiped thereon.

Figure 32:
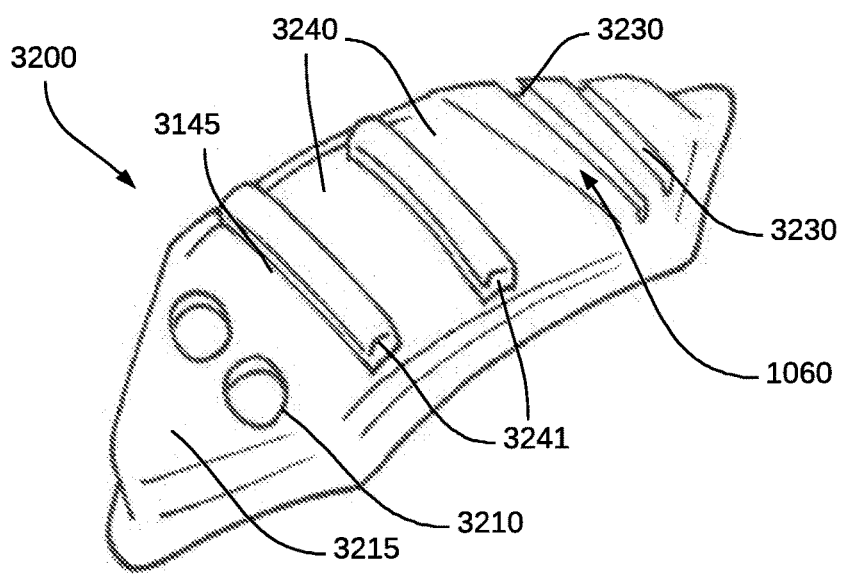

FIG. 32 shows a workspace platform 3200, which is configured for use with orthodontics, in accordance with an embodiment. Like previously described embodiments, workspace platform 3200 includes circular wells 3210 adjacent to a work surface 3215, as well as tapered channels 3230 for accommodating tools, such as microbrushes, therein. Additionally, workspace platform 3200 includes adhesive bands 3240 separated by bars 3241. Adhesive bands 3240 can be used to temporarily hold loose components, such as brackets, elastics, bands, and wires, which are commonly used in orthodontics. Bars 3241 can also be used to temporarily attach clips, clamps, and other torsion components.

Figure 33:
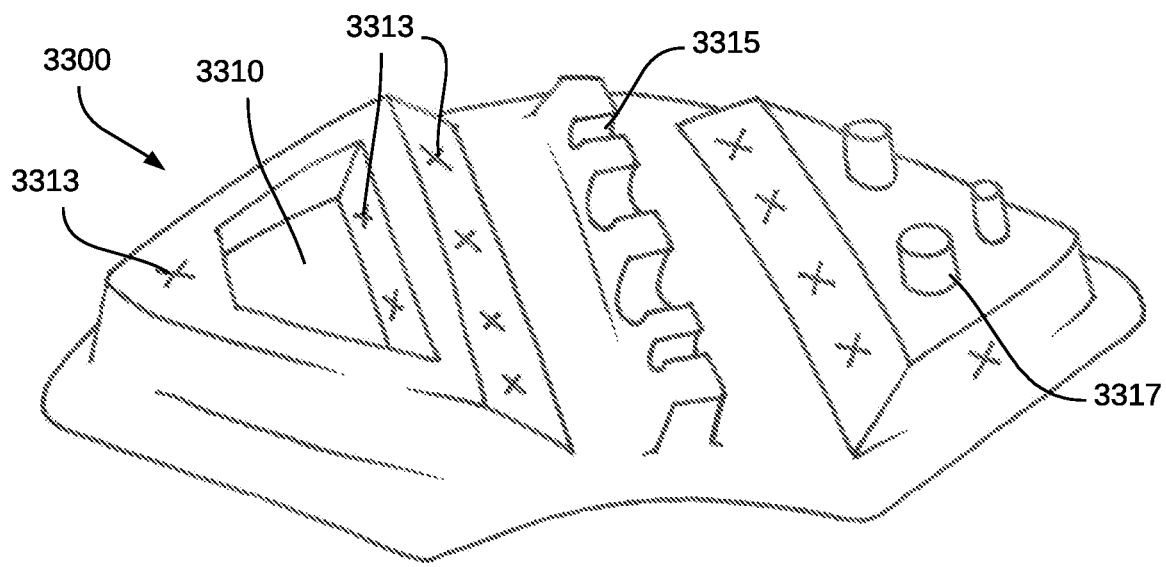

FIG. 33 shows a workspace platform 3300 including features that are useful in implantology applications. Workspace platform 3300 includes a mixing well 3310, which is suitable for mixing materials or storing small components. Workspace platform 3300 also includes a plurality of retention features 3313, which are similar to retention feature 1905 in FIG. 19. In an example, retention features 3313 are x-shaped openings into which small components, such as healing collars, transfers, drills, wedges, matrices, drivers, screws, and others. Furthermore, workspace platform 3300 includes a plurality of slots 3315, which can also be used for storing larger diameter components, such as drills, collars, transfers, and matrices. Such components can also be temporarily held on a plurality of columns 3317.

Figure 34:
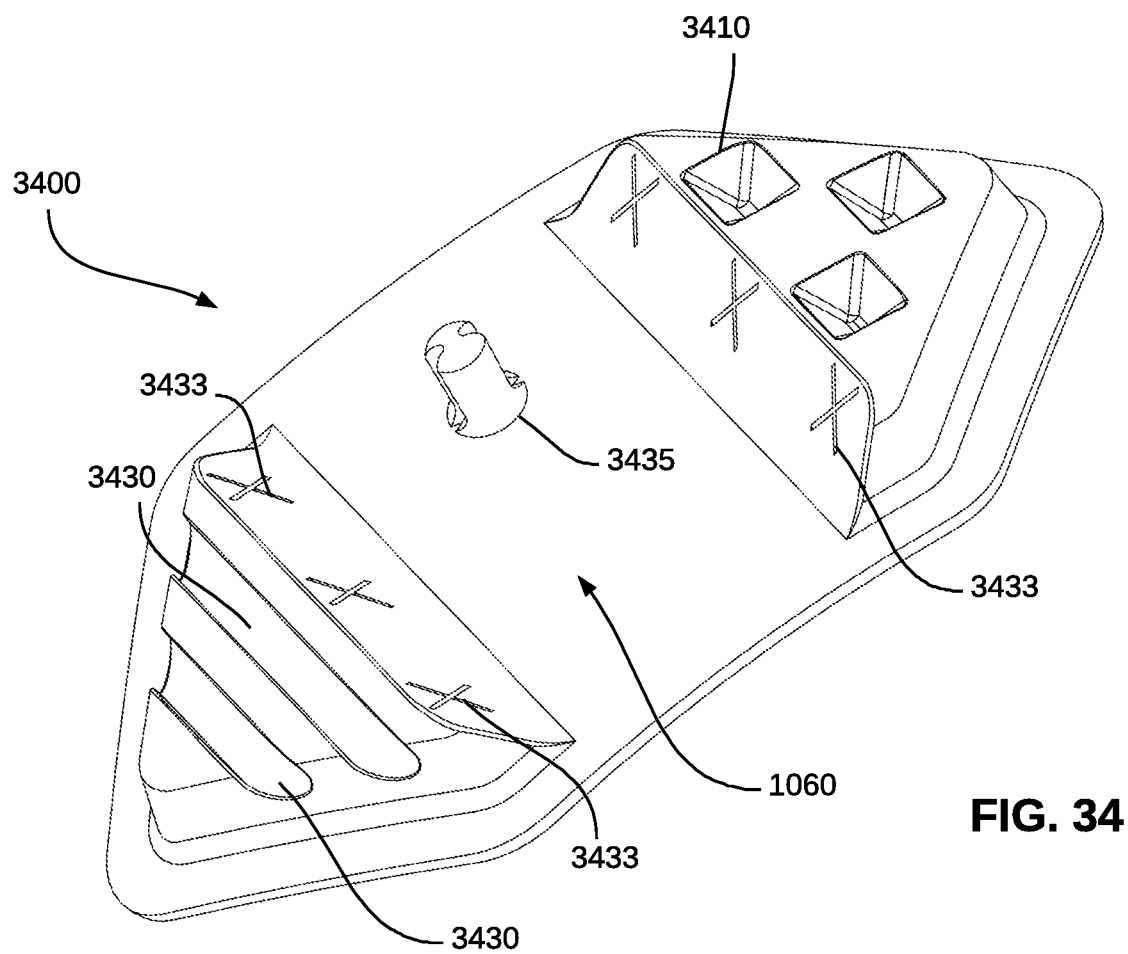

A mechanical drawing of still another variation of a workspace platform is shown in FIG. 34. A workspace platform 3400 includes a plurality of trapezoidal wells 3410, a work surface 3420, channels 3430, and retention features 3433, similar to those described previously. Workspace platform 3400 also includes a ring clamp holder 3435, which is configured as a convenient place for temporarily attaching one or more ring clamps or matrix rings, which are commonly used in restorative dentistry.

Yet another version of a workplace platform is shown in FIG. 35. While in some endodontics applications, gradations printed onto the workplace platform (e.g., as shown in FIG. 31) are sufficient for measuring relative sizes or distances. However, in certain use scenarios requiring more precise measurements, a user may prefer to use, for example, a calibrated metal ruler as the measurement standard. In addition to some of the features of workspace platform 3100 for endodontics, a workspace platform 3500 includes a slot 3520 and a set of tabs 3530 for accommodating a ruler therein.

FIGS. 36 and 37 show different views of still another utility hand strap including a rotation prevention feature, in accordance with an embodiment. FIG. 36 shows a dorsal view of a utility hand strap 3600 worn on a hand 3605. Utility hand strap 3600 includes a dorsal portion 3610, onto which a workplace platform can be attached. While dorsal portion 3610 is shown in FIG. 36 as a smooth layer, attachment features, such as those shown in FIGS. 7, 9, and 22, can be incorporated therein. Utility hand strap 3600 also includes a flap 3620, which includes attachment features such as a hook-and-loop or snaps (not shown) for attaching utility hand strap 3600 around hand 3605. Utility hand strap 3600 further includes an anti-rotation feature 3630, which goes around a middle finger 3650 of hand 3605.

Further details of anti-rotation feature 3630 is shown in FIG. 37, which illustrates a ventral view of utility hand strap 3600 and hand 3605. A ventral portion 3640 can be, for example, formed of a flexible material that conforms to the shape of hand 3605. Anti-rotation feature 3630, in accordance with an embodiment, is a flexible ring configured to fit onto middle finger 3635. Alternatively, the anti-rotation feature can be configured to fit onto one or more other figures of the hand. Also, although anti-rotation feature 3630 is shown to be attached to utility hand strap 3600 on dorsal portion 3610, the anti-rotation feature can be attached to ventral portion 3640 as well. Anti-rotation feature 3630 reduces rotation of utility hand strap 3600 around hand 3605, while providing additional stability for workspace platforms attached to the utility hand strap.

Figure 38:
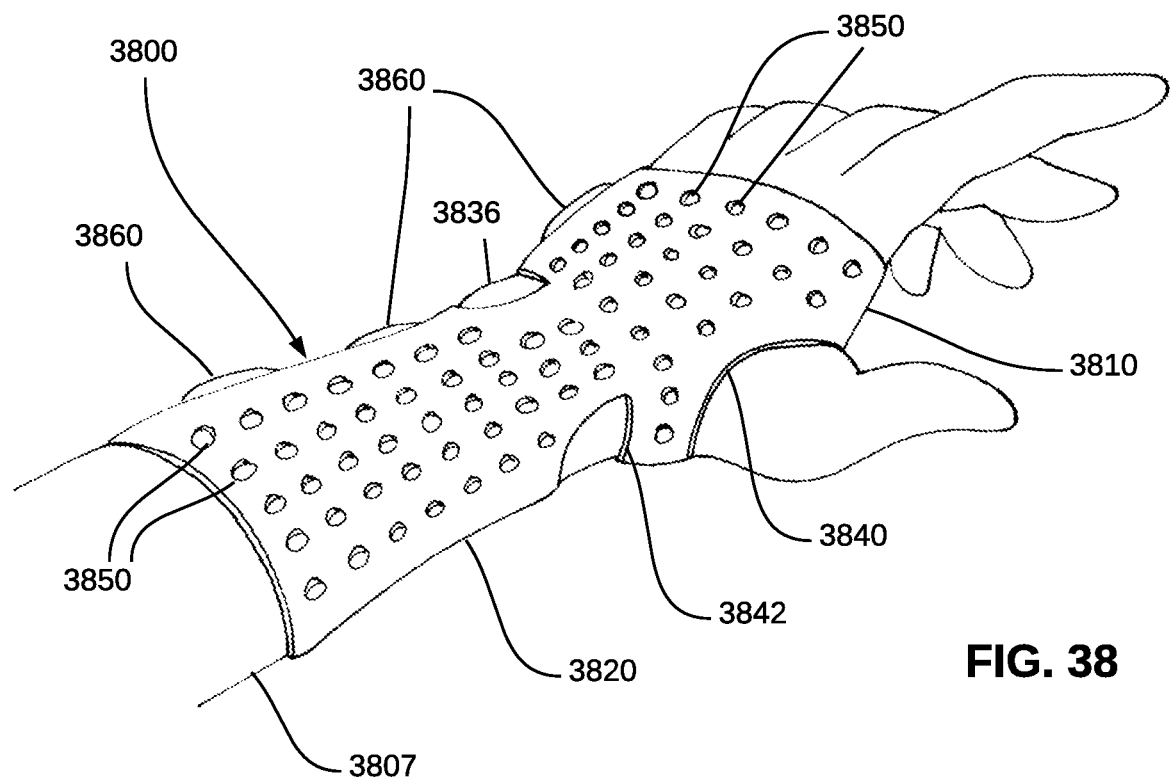
FIGS. 38 and 39 illustrate different views of a utility arm strap, in accordance with an embodiment
Figure 39:
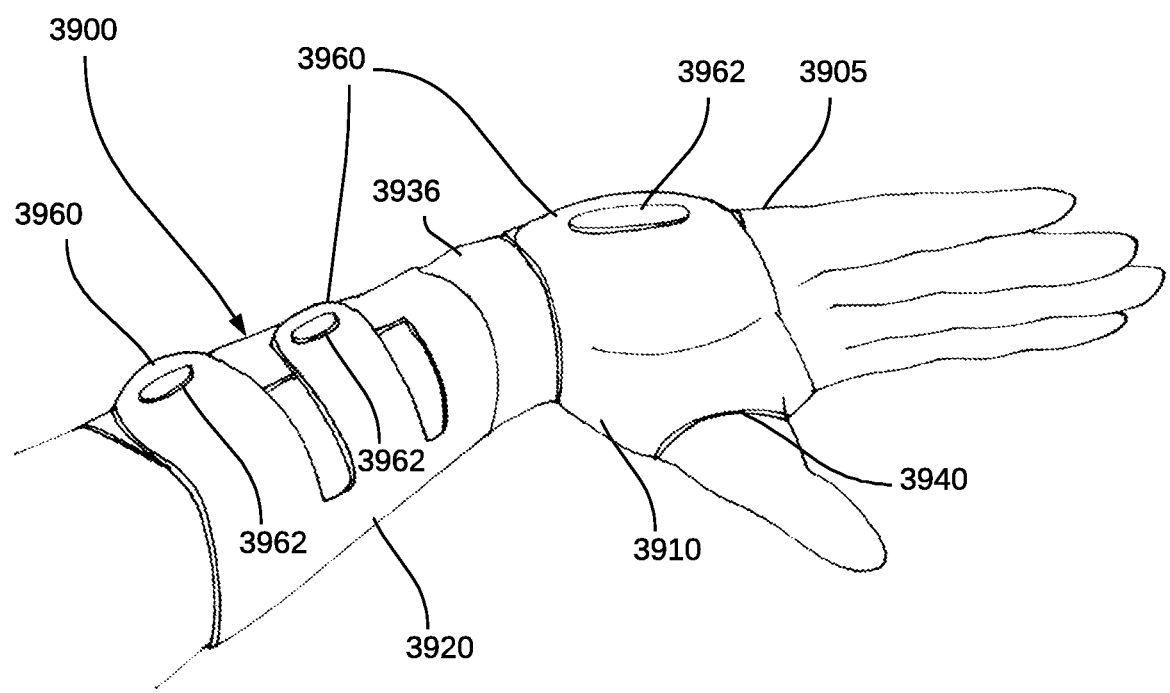

FIGS. 38 and 39 illustrate different views of a utility arm strap, in accordance with an embodiment. FIG. 38 shows a utility arm strap 3800 worn on a left hand 3805 and left arm 3807. In accordance with an embodiment, utility arm strap 3800 extends superiorly from a metacarpal area of left hand 3805, both dorsal and ventral, and terminates inferiorly to the head of the radius and ulna within left arm 3807. Optionally, utility arm strap 3800 can be longer or shorter than is shown in FIGS. 38 and 39. Utility arm strap 3800 includes a hand portion 3810, which is similar to the previously described utility hand straps, and an arm portion 3820, which extends along left arm 3807 below left wrist 3830 toward the left elbow (not shown). Hand portion 3810 includes a thumb hole 3840, and a cut-out 3842 is configured such that utility arm strap 3800 allows free motion of left hand 3805 at left wrist 3830. Utility arm strap 3800 also includes a plurality of attachment features 3850 throughout the dorsal side. Plurality of attachment features 3850 can alternatively be limited to just hand portion 3810 or arm portion 3820, or different types of attachment features, such as embedded magnets, attachment holes, and others, can be incorporated into different parts of utility arm strap 3800. Furthermore, a plurality of straps 3860 are located on the medial side of hand portion 3810 and arm portion 3820 for securing utility arm strap 3800 around left hand 3805 and left arm 3807. Straps 3860 can be, for example, adjustable fasteners, in accordance with an embodiment.

The strap side of a utility arm strap is illustrated in FIG. 39. A utility arm strap 3900 is configured to be worn on a right hand 3905 and a right arm 3907. Utility arm strap 3900 includes a hand portion 3910 and an arm portion 3920, and a right wrist 3936 is left free for flexion. A plurality of flaps 3960 are configured to work with elongated tabs 3962 to secure utility arm strap 3900 around right hand 3905 and right arm 3907.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention.

Accordingly, many different embodiments stem from the above description and the drawings. It will be understood that it would be unduly repetitious and obfuscating to literally describe and illustrate every combination and subcombination of these embodiments. As such, the present specification, including the drawings, shall be construed to constitute a complete written description of all combinations and subcombinations of the embodiments described herein, and of the manner and process of making and using them, and shall support claims to any such combination or subcombination.

For instance, the utility hand strap can include stabilizing features and provide anti-rotation about the hand. As an example, a retention loop around one of the fingers can help prevent rotation of the utility hand strap around the user's hand. Optionally, support features, such as internal ribs and framework, can be incorporated into the utility hand strap to reduce hand fatigue and injury as well as to improve ergonomics while using the utility hand strap. Both the utility hand strap and the workspace platform should be formed of materials that are resistant to disinfectant chemicals and other materials that are used during a specific application, such as solvents and chemicals commonly used in dentistry. The utility hand strap and the workspace platform can include functional features that are specifically designed for a particular application, such as restorative dentistry, hygiene, endodontics, orthodontics, periodontics, implantology, cosmetology, veterinary medicine, plastic surgery, and other industries that require the manipulation of small objects and devices with the hands.

The use of the workspace platform can reduce the time in performing manual procedures and tasks, while reducing errors due to repetitive movements and transfer of materials between separate work surfaces. For dentistry application, for instance, the use of the workspace platform can help reduce short- and long-term health risks associated with eye strain and postural complications from fatigue, strain, and poor ergonomics. Also, the workspace platform embodiments described herein enables the interchangeability of workspace platforms so as to allow the execution of a series of procedures, using a variety of workspace platforms, without having to completely reset between procedures. For example, two or more workspace platforms can be prepared ahead of time such that, in the course of a complicated procedure, the workspace platforms are simply interchanged to meet the needs of specific steps during the procedure, thus saving time and reducing error.

Additionally, texture variations can be provided on the workplace platform for aiding in different applications. For example, a smooth or polished surface in a mixing well provided on a workplace platform allows a user to efficiently use up solutions or pastes held in the mixing well, thus reducing waste. Alternatively, a striated, bumpy, or rough surface texturing can be provided, for instance, to prevent less viscous solvents from spilling out of the mixing well or to provide a more effective wiping surface to clean off tools. Additional surface variations are contemplated, and are considered to be a part of this disclosure.

In the specification, there have been disclosed embodiments of the invention and, although specific terms are employed, they are used in a generic and descriptive sense only and not for purposes of limitation. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A modular workspace platform system for providing a mobile work surface for a user, the system comprising:
   a workspace platform attachable to a location specified by the user,
   wherein the workspace platform includes a first compact work surface for use in performing at least one manual task including temporarily storing a material, mixing two or more materials, temporarily supporting a tool, and providing a tool cleaning surface,
   wherein the workspace platform further includes a second compact work surface located in a middle section of the workspace platform, the second compact work surface being pliable such that the workspace platform flexibly conforms to a contour of the location at which the workspace platform is attached,
   wherein the second compact work surface is configured for use in at least one of temporarily storing a material and mixing two or more materials thereon, and
   wherein the workspace platform is configured to be attachable to a backside of a hand.

2. The system of claim 1, wherein the first compact work surface includes at least one of a trough, a tapered channel, a tool insertion slot, a wipe holder, a textured surface configured as the tool cleaning surface, a mixing surface, a ruler holder, an adhesive band, and a matrix ring holder.

3. The system of claim 2, wherein the trough is configured for containing at least one of a liquid, a gel, a powder, a foam, and a mechanical component.

4. The system of claim 2, wherein the trough is trapezoidal in shape.

5. The system of claim 1, wherein the hand is covered by a glove, and wherein the workspace platform is configured to be attachable to the glove.

6. The system of claim 1, wherein the workspace platform is formed of a pliable material.

7. The system of claim 1, wherein the workspace platform further includes linear graduations.

8. The system of claim 1, wherein the workspace platform includes an adhesive for attaching to an attachment location.

9. The system of claim 1, wherein the workspace platform is configured to be disposable.

10. The system of claim 1, wherein the workspace platform is configured to be reusable.

11. The system of claim 10, wherein the workspace platform is configured to be compatible with sterilization procedures.

12. The system of claim 1, further comprising a removable hand and/or arm strap for accommodating the workspace platform thereon.

13. The system of claim 12, wherein the removable hand and/or arm strap is configured to be reusable.

14. The system of claim 13, wherein the removable hand and/or arm strap is configured to be compatible with sterilization procedures.

15. The system of claim 12, wherein the removable hand and/or arm strap and the workspace platform include at least one of matingly engaging snaps, magnets, adhesives, and hook-and-loop attachments for removably attaching the workspace platform onto the removable hand and/or arm strap.

16. The system of claim 12, wherein the removable hand and/or arm strap is configured for accommodating hands and/or arms of a variety of sizes.

17. The system of claim 1, wherein the second compact work surface is larger than the first compact work surface.

18. The system of claim 1, wherein the second compact work surface is bendable asymmetrically.

* * * * *